(12) United States Patent
Vardas et al.

(10) Patent No.: US 10,398,350 B2
(45) Date of Patent: Sep. 3, 2019

(54) METHODS AND SYSTEMS FOR PROVIDING A BREATHING RATE CALIBRATED TO A RESONANCE BREATHING FREQUENCY

(71) Applicant: Vardas Solutions LLC, El Dorado Hills, CA (US)

(72) Inventors: Chad Vardas, El Dorado Hills, CA (US); Alex Jones, Carlsbad, CA (US)

(73) Assignee: Vardas Solutions LLC, El Dorado Hills, CA (US)

( * ) Notice: Subject to any disclaimer, the term of this patent is extended or adjusted under 35 U.S.C. 154(b) by 0 days.

(21) Appl. No.: 16/006,558

(22) Filed: Jun. 12, 2018

(65) Prior Publication Data

US 2018/0289285 A1 Oct. 11, 2018

Related U.S. Application Data

(63) Continuation-in-part of application No. 15/428,115, filed on Feb. 8, 2017.

(60) Provisional application No. 62/292,450, filed on Feb. 8, 2016.

(51) Int. Cl.
*A61B 5/0205* (2006.01)
*A61B 5/08* (2006.01)
*A61B 5/024* (2006.01)
*A61B 5/00* (2006.01)

(52) U.S. Cl.
CPC .......... *A61B 5/0816* (2013.01); *A61B 5/0205* (2013.01); *A61B 5/02405* (2013.01); *A61B 5/7242* (2013.01)

(58) Field of Classification Search
CPC ..... A61B 5/02; A61B 5/0205; A61B 5/02405; A61B 5/02438; A61B 5/486; G09B 19/003
See application file for complete search history.

(56) References Cited

U.S. PATENT DOCUMENTS 5,682,898 A 11/1997 Aung et al.
6,212,427 B1 4/2001 Hoover et al.
(Continued)

FOREIGN PATENT DOCUMENTS

CN 103211603 A 7/2013
CN 103690166 A 4/2014
(Continued)

OTHER PUBLICATIONS

International Search Report, PCT/US2018/037156, dated Sep. 21, 2018 (Year: 2018).*
(Continued)

*Primary Examiner* — Allen Porter
(74) *Attorney, Agent, or Firm* — Dergosits & Noah LLP

(57) ABSTRACT

A target respiration rate is determined for a user where, when the user breathes at the target rate, the user's vagal tone is improved, which provides a physiological benefit to the user, e.g., stress reduction without drug intervention. The user is directed to breathe at different rates while heart rate and breathing rate are measured. A value representative of vagal tone is generated from the measured heart and breathing rates for each directed breathing rate. The breathing rate that produced the lowest generated vagal tone value is determined to be the user's target respiration rate.

14 Claims, 14 Drawing Sheets

(56) References Cited

U.S. PATENT DOCUMENTS

| | | | |
|---|---|---|---|
| 6,305,943 B1 * | 10/2001 | Pougatchev | A61B 5/486 434/238 |
| 6,358,201 B1 | 3/2002 | Childre et al. | |
| 6,377,845 B1 | 4/2002 | Kinast | |
| 6,665,611 B1 | 12/2003 | Oran et al. | |
| 6,836,681 B2 * | 12/2004 | Stabler | A61B 5/02405 600/26 |
| 7,117,032 B2 | 10/2006 | Childre et al. | |
| 7,163,512 B1 | 1/2007 | Childre et al. | |
| D554,266 S | 10/2007 | Striepe et al. | |
| 7,462,151 B2 | 12/2008 | Childre et al. | |
| 7,618,378 B2 * | 11/2009 | Bingham | A61B 5/486 600/529 |
| 7,691,049 B2 * | 4/2010 | Wood | A61B 5/0059 600/26 |
| 8,066,637 B2 | 1/2011 | Childre et al. | |
| 8,002,711 B2 | 8/2011 | Wood et al. | |
| 8,123,696 B2 | 2/2012 | Childre et al. | |
| 8,301,232 B2 | 10/2012 | Albert et al. | |
| 8,306,621 B2 | 11/2012 | Kim et al. | |
| 8,509,882 B2 | 8/2013 | Albert et al. | |
| 8,523,758 B1 | 9/2013 | Kirby et al. | |
| 8,543,197 B2 | 9/2013 | Striepe et al. | |
| 8,700,137 B2 | 4/2014 | Albert | |
| 8,764,673 B2 | 7/2014 | McCraty et al. | |
| 8,936,556 B2 | 1/2015 | Lee et al. | |
| 8,938,288 B2 | 1/2015 | Wood et al. | |
| 9,026,202 B2 | 5/2015 | Albert | |
| 9,113,807 B2 | 8/2015 | Koyrakh et al. | |
| 9,220,430 B2 | 12/2015 | Albert | |
| 9,247,911 B2 | 2/2016 | Galloway et al. | |
| 9,254,092 B2 | 2/2016 | Albert et al. | |
| 9,254,095 B2 | 2/2016 | Galloway et al. | |
| 9,351,654 B2 | 5/2016 | Albert | |
| 9,420,956 B2 | 8/2016 | Gopalakrishnan et al. | |
| 9,572,499 B2 | 2/2017 | Gopalakrishnan et al. | |
| 9,579,062 B2 | 2/2017 | Albert | |
| 9,610,017 B2 | 4/2017 | Casal et al. | |
| 9,699,528 B2 | 7/2017 | Dixit et al. | |
| 9,830,832 B2 * | 11/2017 | Warren | G09B 19/003 |
| 9,913,612 B2 | 3/2018 | Banet et al. | |
| 2005/0033189 A1 | 2/2005 | McCraty et al. | |
| 2005/0124906 A1 | 6/2005 | Childre et al. | |
| 2005/0209504 A1 | 9/2005 | Elliott et al. | |
| 2005/0288601 A1 * | 12/2005 | Wood | A61B 5/0059 600/513 |
| 2007/0021675 A1 | 1/2007 | Childre et al. | |
| 2007/0270668 A1 | 11/2007 | Childre et al. | |
| 2007/0299354 A1 | 12/2007 | Striepe et al. | |
| 2009/0137915 A1 | 5/2009 | Childre et al. | |
| 2009/0281400 A1 | 11/2009 | Farazi et al. | |
| 2010/0041967 A1 | 2/2010 | McCraty et al. | |
| 2011/0301435 A1 | 2/2011 | Albert et al. | |
| 2011/0301439 A1 | 12/2011 | Albert et al. | |
| 2012/0172689 A1 | 7/2012 | Albert et al. | |
| 2013/0197320 A1 | 8/2013 | Albert et al. | |
| 2014/0050321 A1 | 2/2014 | Albert et al. | |
| 2014/0066798 A1 | 3/2014 | Albert | |
| 2014/0128758 A1 | 5/2014 | Galloway et al. | |
| 2014/0194760 A1 | 7/2014 | Albert | |
| 2014/0221859 A1 | 8/2014 | Albert | |
| 2014/0228665 A1 | 8/2014 | Albert | |
| 2014/0276162 A1 | 9/2014 | Albert et al. | |
| 2015/0018660 A1 | 1/2015 | Thomson et al. | |
| 2015/0018702 A1 | 1/2015 | Galloway et al. | |
| 2015/0073285 A1 | 3/2015 | Albert et al. | |
| 2015/0087952 A1 | 3/2015 | Albert et al. | |
| 2015/0164349 A1 | 6/2015 | Gopalakrishnan et al. | |
| 2015/0265164 A1 | 9/2015 | Gopalakrishnan et al. | |
| 2015/0297134 A1 | 10/2015 | Albert et al. | |
| 2015/0317885 A1 | 11/2015 | Ramstein et al. | |
| 2015/0320328 A1 | 11/2015 | Albert | |
| 2016/0074674 A1 | 3/2016 | Kohli et al. | |
| 2016/0184518 A1 | 6/2016 | Freeman et al. | |
| 2016/0234572 A1 | 8/2016 | Dixit | |
| 2016/0235319 A1 | 8/2016 | Albert | |
| 2016/0242665 A1 | 8/2016 | Galloway et al. | |
| 2016/0242697 A1 | 8/2016 | Albert | |
| 2016/0249823 A1 | 9/2016 | Galloway et al. | |
| 2016/0331247 A1 | 11/2016 | Albert | |
| 2017/0325700 A1 * | 11/2017 | Lane | G16H 50/30 |
| 2018/0312167 A1 | 11/2018 | Kundu | |

FOREIGN PATENT DOCUMENTS

| | | |
|---|---|---|
| KR | 20150099430 A | 8/2015 |
| WO | 0028892 A1 | 5/2000 |
| WO | 2000051677 A2 | 9/2000 |
| WO | 2005015157 A2 | 2/2005 |
| WO | 2005044092 A2 | 5/2005 |
| WO | 2010014170 A1 | 2/2010 |
| WO | 2011156374 A2 | 12/2011 |
| WO | 2012158190 A1 | 11/2012 |
| WO | 2013112979 A1 | 8/2013 |
| WO | 2014028899 A1 | 2/2014 |
| WO | 2014036436 A1 | 3/2014 |
| WO | 2014074913 A1 | 5/2014 |
| WO | 2014107700 A1 | 7/2014 |
| WO | 2014145927 A1 | 9/2014 |
| WO | 2014172451 A1 | 10/2014 |
| WO | 2015035251 A1 | 3/2015 |
| WO | 2015089484 A1 | 6/2015 |
| WO | 2015164404 A1 | 10/2015 |
| WO | 2015171764 A1 | 11/2015 |
| WO | 2016183515 A1 | 11/2016 |

OTHER PUBLICATIONS

International Written Opinion, PCT/US2018/037156, dated Sep. 21, 2018 (Year: 2018).*

Peace of mind in your pocket, Jun. 11, 2018, https://www.alivecor.com, Retrieved Jul. 31, 2018, pp. 1-5.

Compare Apple Watch Models, Jun. 6, 2018, https://www.apple.com/watch/compare/, Retrieved Jun. 29, 2018, p. 1-4.

Apple Watch Series 3, Jun. 6, 2018, www.apple.com/watch, Retrieved Jun. 29, 2018, pp. 1-6.

Compare Apple Watch Models, Jun. 7, 2018, https://www.apple.com/watch/compare/, Retrieved Jun. 29, 2018, p. 1-3.

Linea No. 10, Apr. 15, 2018, https://www.caeden.com, Retrieved Jul. 31, 2018, pp. 1-2.

The Caeden Sona Connected Bracelet for Mind and Body, Jan. 12, 2018, https://www.caeden.com:80/sona/, Retrieved Jul. 31, 2018, pp. 1-6.

Fibit alta HR, Move to the beat of you, Jun. 9, 2018, https://www.fibit.com/altahr, Retrieved Jul. 26, 2018, pp. 1-7.

Fitbit motivates you to reach your health and fitness goals by tracking your activity, exercise, sleep, weight and more, Jun. 11, 2018, https://www.fabit.com/home, Retrieved Jul. 26, 2018, pp. 1-3.

Track, analyze and share your data, Jun. 8, 2018, https://buy.garmin.com/en-US/US/wearabletech/wearables/c10001-c10002-p1.html, Retrieved Jul. 31, 2018, pp. 1-3.

Take Charge of Flow You Feel, Release Stress/Find Balance/Build Resilience, Jun. 7, 2018, https://store.heartmath.com/, Retrieved Jul. 26, 2018, pp. 1-5.

The Journey of Happiness, Dec. 3, 2017, http://www.iheha.com:8/hk-en/index.php, Retrieved Jul. 31, 2018, pp. 1-3.

Wearable relief, rack your stress, train for relief, Jun. 11, 2018, https://getlief.com, Retrieved Jul. 26, 2018, pp. 1-4.

When you're calm you'll hear peaceful weather sounds, Jun. 5, 2018, https://www.choosemuse.com, Retrieved Jul. 26, 2018, pp. 1-5.

Lead a healthier, happier life by managing your stress, Feb. 19, 2018, https://thepip.com/en-us, Retrieved Jul. 31, 2018, pp. 1-6.

Breathe better, Sit better, Feel better, with Prana, May 18, 2018, http://prana.co/, Retrieved Jul. 31, 2018, pp. 1-12.

Make Your Clothes Smart, Jun. 7, 2018, https://www.spire.io/, Retrieved Jul. 26, 2018, pp. 1-3.

(56) References Cited

OTHER PUBLICATIONS

Thync's bioelectronics wearable shows promise in psoriasis pilot, Oct. 9, 2017, http://fiercebiotech.com:8/medtech/thync-s-bioelectronics-wearable-shows-promise-psoriasis-pilot, Retrieved Jul. 31, 2018, pp. 1-3.
Breakthrough Bioelectronic Therapies, Jun. 10, 2018, https://www.thync.com/, Retrieved Jul. 31, 2018, pp. 1-3.
Want to Win a Free Set of Touchpoints?, Feb. 24, 2018, https://www.thetouchpointsolution.com, Retrieved Jul. 26, 2018, pp. 1-5.
The world's first stress balancing bracelet, Oct. 4, 2017, http://thewellbe.com/, Retrieved Jul. 31, 2018, pp. 1-8.
International Search Report and Written Opinion, PCT/US17/17065, dated May 16, 2017, 22 pages.
Kohli et al., Prototype development of an electrical impedance based simultaneous resopiratory and cardiac monitoring system for gated radiotherapy, BioMedical Engineering Online (2014) 13:144, http://www.biomedical-engineering-online.com/content/13/1/144.
Trobec et al., Two Proximal Skin Electrodes—A Respiration Rate Body Sensor, Sensors (2012) 12, pp. 13813-13828; www.mdpi.com/journal/sensors.
Google translation for CN103690166 A, https://patents.google.com/patent/CN103690166B/en, retrieved Feb. 27, 2019, 6 pages.

\* cited by examiner

METHODS AND SYSTEMS FOR PROVIDING A BREATHING RATE CALIBRATED TO A RESONANCE BREATHING FREQUENCY

CROSS-REFERENCE TO RELATED CASES

The present application in a continuation-in-part of U.S. patent application Ser. No. 15/428,115, entitled "STRESS MANAGEMENT USING BIOFEEDBACK," filed on Feb. 8, 2017, which claims priority to U.S. Provisional Patent Application No. 62/292,450, entitled "WEARABLE APPARATUS WITH BIOFEEDBACK," filed on Feb. 8, 2016, which are both hereby incorporated by reference.

TECHNICAL FIELD

The present disclosure relates to the field of stress reduction technology, including, more particularly, to methods and systems for reducing stress by training a person to breathe at a breathing rate that is based on that person's resonance frequency.

BACKGROUND

It is a common problem for an individual to suffer from stress and anxiety. By some current estimates, 234 million Americans regularly experience psychological symptoms of stress, 64 million Americans are diagnosed with an anxiety disorder, and 54 million Americans are prescribed antidepressants or anti-anxiety drugs.

The benefits of antidepressants and anti-anxiety drugs are undeniable, but the treating of stress-related disorders with such medications can have a down-side in the form of drug abuse and addiction.

In the United States alone, it is currently estimated that more than 15 million people abuse prescription drugs and that this abuse results in 45% of the drug-related deaths in the U.S.—more than heroin, methamphetamine, and cocaine combined.

Furthermore, even in the absence of drug abuse, a stigma is often associated with the mere taking of medication for stress or anxiety.

For these reasons it would be desirable to have a system and method to reduce stress and anxiety that did not require drugs, such as antidepressants or anti-anxiety drugs.

BRIEF DESCRIPTION OF THE DRAWINGS

The embodiments are illustrated by way of example and not limitation in the figures of the accompanying drawings, in which like references indicate similar elements, and in which.

DETAILED DESCRIPTION

An embodiment provides a system and method for reducing stress and anxiety that is based on training the person to breathe at a rate that increases vagal tone. This embodiment does not require any drugs, which eliminates any potential of the stigma or drug abuse associated with medication.

Embodiments make use of the following physiology. The parasympathetic nervous system is controlled by the vagus nerve. Vagal tone is an index of how well the vagus nerve is causing the body to relax. Vagal tone is measured by Heart Rate Variability (HRV), and is best when individuals breathe at their resonance breathing frequency (or "resonance breathing rate"). HRV is the variation of the time intervals between heart beats. An increase in HRV is desirable because it is indicative of a heart rate that is variable and responsive to physiological demands. Respiratory Sinus Arrhythmia (RSA) is the synchrony of respiration and heart rates. Heart rate increases upon inhalation and decreases upon exhalation. RSA occurs when HRV is in synchrony with respiration, shown when variability on an ECG is shortened during inspiration and prolonged during expiration. Every person has a unique breathing rate, known as his or her resonance breathing frequency, which when achieved by that person improves HRV, RSA, and vagal tone as much as possible. To attain the optimal resonance state, it has been determined that a person should usually breathe at their resonance frequency for approximately one minute.

Thus, embodiments of the methods and devices that implement the methods provide desirable biofeedback to users, giving them insight into their parasympathetic nervous system. The methods and systems use adaptive intelligence and change the feedback given and biometrics measured based on real time factors. Embodiments help users to optimize the beneficial effect of breathing on the body by providing the user with a target breathing rate—the user's specific resonance breathing frequency—and by providing the user with feedback that trains the user to breathe at that frequency.

Figure 1A:
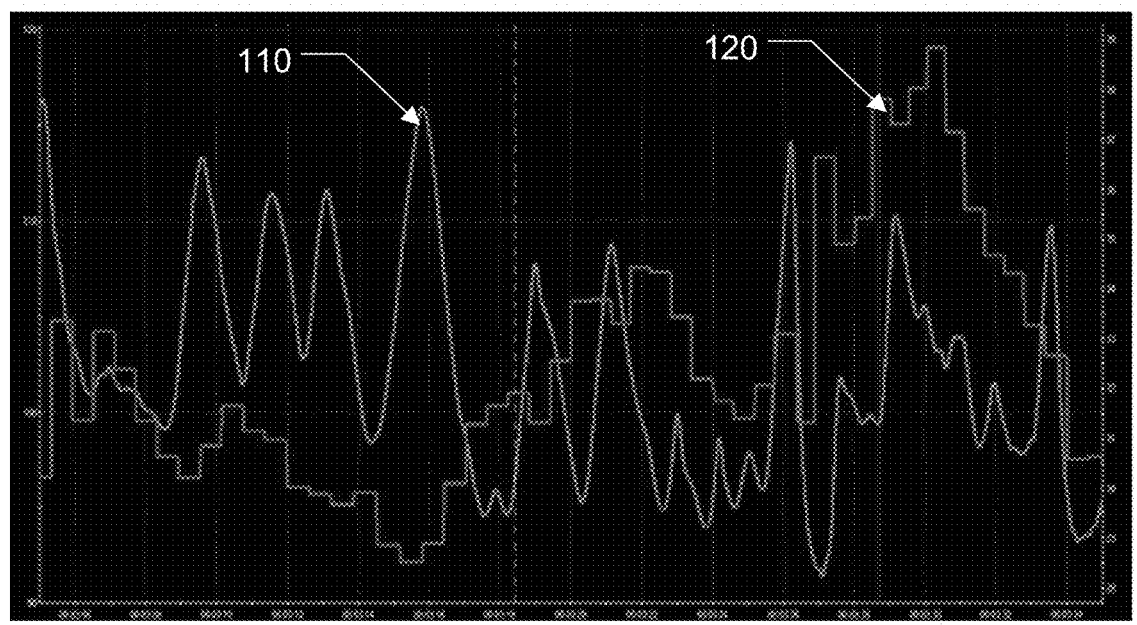
FIG. 1A and FIG. 1B are exemplary charts each depicting a heart rate and a standard breathing rate plotted against time.
Figure 1B:
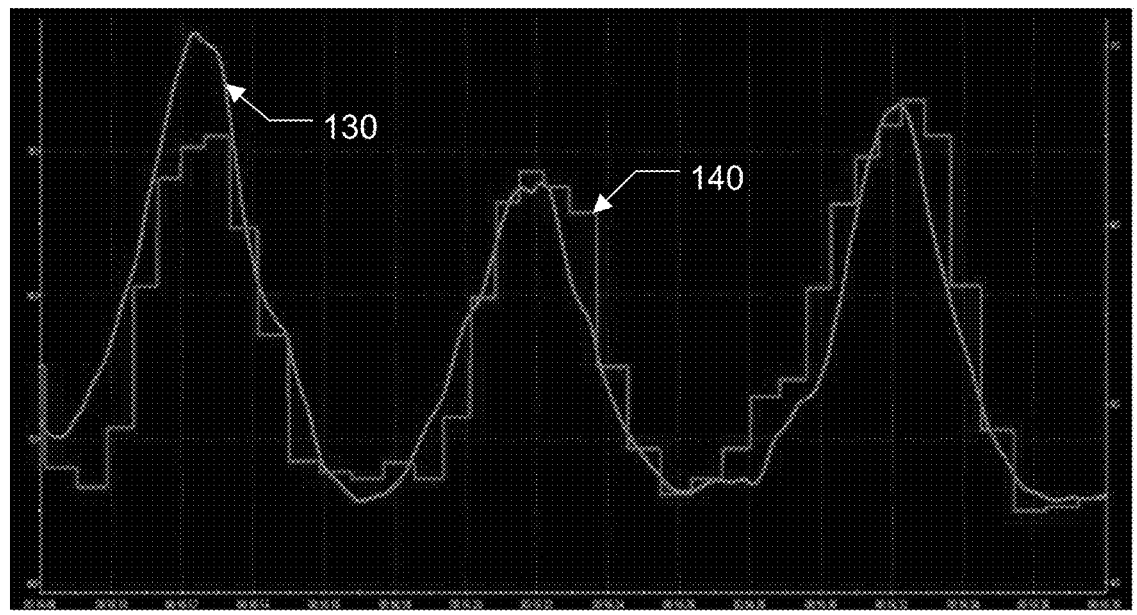

FIG. 1A is an exemplary chart depicting a heart rate 110 and a standard (or "non-optimal") breathing rate 120 plotted against time. In FIG. 1A, there is no obvious correlation between heart rate 110 and standard breathing rate 120. FIG. 1B is an exemplary chart depicting a heart rate 130 and an optimal breathing rate 140 plotted against time. FIG. 1B shows the synchronization of heart rate 130 and optimal breathing rate 140. To reach this state, it has been determined optimal breathing rate 140 should be practiced for approximately one minute. FIG. 1B depicts an example of respiratory sinus arrhythmia (RSA) in that heart rate 130 increases with inspiration, as shown by optimal breathing rate 140 increasing, and heart rate 130 decreases with expiration, as shown by optimal breathing rate 140 decreasing. In FIGS. 1A and 1B the y-axes represent raw data and have been adjusted to better illustrate the correlation, or lack thereof.

However, the average person does not know what their optimal, resonance breathing rate is. Nor do they have a way to determine it.

Figure 2:
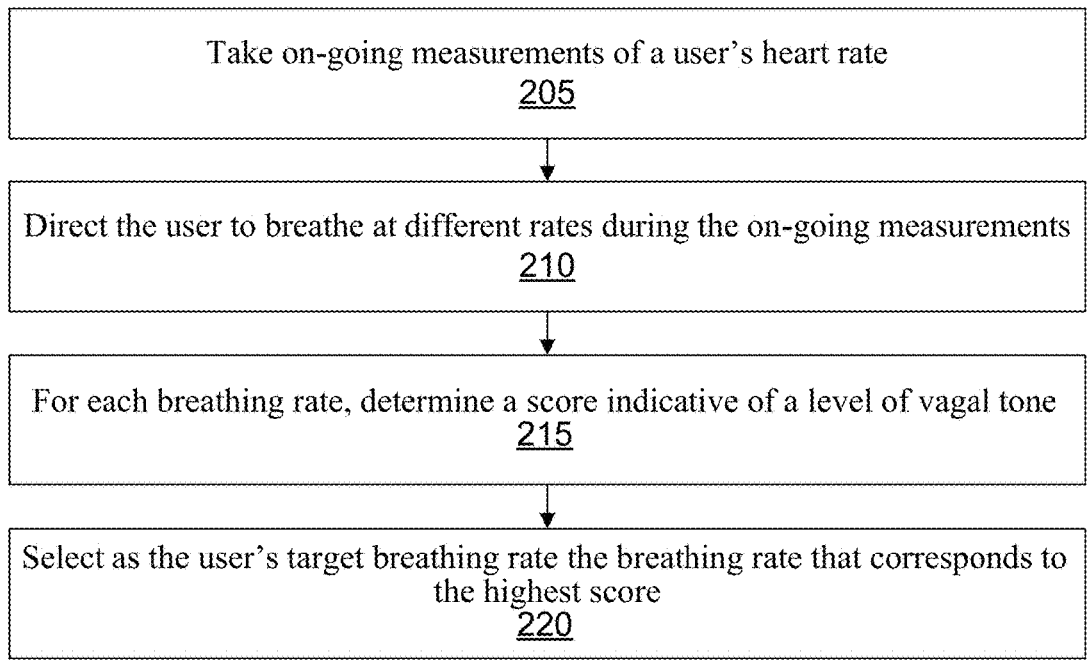
FIG. 2 is an exemplary block diagram of an embodiment of a method for determining a resonance breathing frequency.

FIG. 2 is an exemplary block diagram of an embodiment of a method 200 for determining a person's resonance breathing frequency. To determine a resonance breathing rate, in step 205, on-going measurements are taken of a person's heart rate. In step 210, the person is directed to breathe at different rates during the on-going measurements. In step 215, for each breathing rate, a VT Score is determined that is indicative of a level of vagal tone (a "VT Score"). And in step 220, the breathing rate that corresponds to the lowest VT Score is selected as the person's target breathing rate. In this embodiment, that selected target breathing rate is considered to be the person's resonance breathing rate.

In an embodiment, the person's HRV may be measured with a true electrocardiogram (ECG).

In an embodiment, the precision of the determined target breathing rate may be increased by performing the method iteratively. That is, in a first performance of method 200, the gap in step 210 between different directed breathing rates may be relatively large such that the greatest determined score in step 215 provides an indication of vagal tone (a "VT Score") for a general range of breathing rates in which an eventual target breathing rate is located. In a subsequent iteration of method 200, the steps of FIG. 2 are repeated and the precision of the resulting target breathing rate increased by dividing the general range determined in the first iteration into smaller segments by using smaller gaps between the directed breathing rates in step 210 of the second iteration. Thus, method 200 may be performed an arbitrary number of times to increase the precision of the determined resonance breathing frequency to a desired level.

In an embodiment, the precision of the determined target breathing rate may be improved by reducing the size of the gap between directed breathing rates.

In an embodiment, the target breathing rate may be modified with the determination of a pause (or "hold") that, when inserted in a respiratory cycle after inhalation and also after exhalation, increases the measurement of vagal tone.

Figure 3:
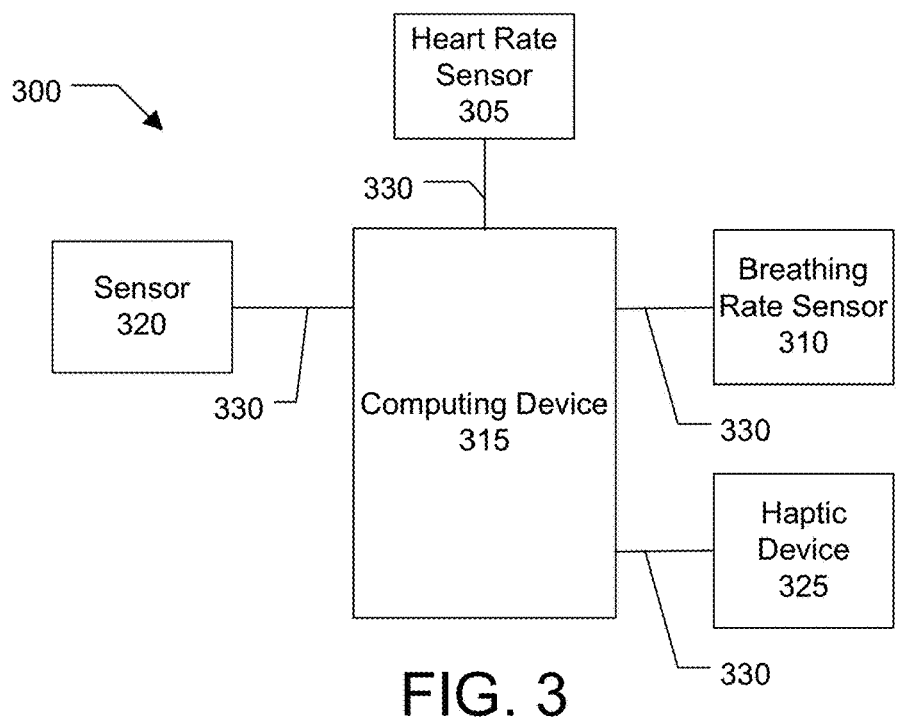
FIG. 3 is a simplified, exemplary block diagram of an embodiment of a system for implementing the embodiments of the methods disclosed herein.

FIG. 3 is a simplified, exemplary block diagram of an embodiment of a system 300 for implementing the embodiments of the methods disclosed herein. System 300 includes a number of sensors, e.g., a heart rate sensor 305 and a breathing rate sensor 310, for developing data regarding a user. Sensors 305, 310, and 320 are in communication with a computing device 315. Computing device 315 is further in control of a haptic device 325 and a buzzer or speaker (not shown) for communicating with the user. Computing device 315 is optionally referred to within as a Biometric Analysis Device.

Heart rate sensor 305 may be, e.g., a plurality of sensors sufficient to produce an electrocardiogram (ECG), a chest-mounted device, or a wrist-mounted device, so long as the device provides heart rate data with sufficient accuracy and precision. Breathing rate sensor 310 may be, e.g., a pneumograph measuring the velocity and force of chest movements or a may be sensors determining a respiratory rate using other input, such as impedance-based sensors. Sensor 320 is representative of additional sensors that may be included, such as sensors for determining galvanic skin response, temperature, blood pressure, hydration, sleep, exercise activity, brain activity, nutrient levels, or blood analysis. Sensors 305, 310, and 320 supply data to computing device 315 via communication links 330.

Computing device 315 includes a user interface and software, which implement the steps of the method. Computing device receives data from sensors 305, 310, and 320, via communication links 330, which may be hardwire links, optical links, satellite or other wireless communications links, wave propagation links, or any other mechanisms for communication of information. Various communication protocols may be used to facilitate communication between the various components shown in FIG. 3. Distributed system 300 in FIG. 3 is merely illustrative of an embodiment and does not limit the scope of the systems and methods as recited in the claims. In an embodiment, the elements of system 300 are incorporated into a single, wearable Biometric Analysis Device. One of ordinary skill in the art would recognize other variations, modifications, and alternatives. For example, more than one computing device 315 may be employed. As another example, sensors 305 and 310 may be coupled to computing device 315 via a communication network (not shown) or via some other server system.

Computing device 315 is responsible for receiving data from sensors 305, 310, and 320, performing processing required to implement the steps of the methods, and for interfacing with the user. In some embodiments, the processing required is performed by computing device 315. In such embodiments, computing device 315 runs an application for receiving user data, performing the steps of the method, and interacting with the user. In other embodiments, computing device 315 may be in communication with a server, which performs the required processing, with computing device 315 being an intermediary in communications between the user and the processing server.

Computing device 315 enables users to access and query information developed by the disclosed methods. Some example computing devices include desktop computers, portable electronic devices (e.g., mobile communication devices, smartphones, tablet computers, laptops) such as the Samsung Galaxy Tab®, Google Nexus devices, Amazon Kindle®, Kindle Fire®, Apple iPhone®, the Apple iPad®, Microsoft Surface®, the Palm Pre™, or any device running the Apple iOS®, Android® OS, Google Chrome® OS, Symbian OS®, Windows Mobile® OS, Windows Phone, BlackBerry® OS, Embedded Linux, Tizen, Sailfish, webOS, Palm OS® or Palm Web OS®; or wearable devices such as smart watches, smart fitness or medical bands, and smart glasses.

Figure 4:
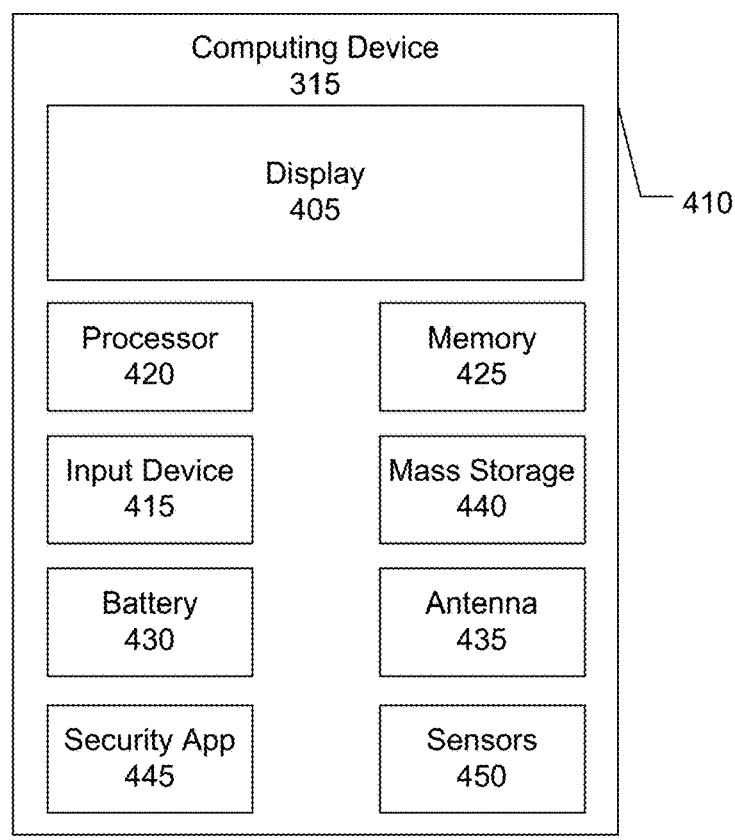
FIG. 4 is an exemplary block diagram of a computing device from the system of FIG. 3.

FIG. 4 is an exemplary block diagram of a computing device 315 from the system of FIG. 3. In an embodiment, a user interfaces with the system through computing device 315, which also receives data and performs the computational steps of the embodiments. Computing device 315 includes a display, screen, or monitor 405, housing 410, input device 415, sensors 450, and a security application 445. Housing 410 houses familiar computer components, some of which are not shown, such as a processor 420, memory 425, battery 430, speaker, transceiver, antenna 435, microphone, ports, jacks, connectors, camera, input/output (I/O) controller, display adapter, network interface, mass storage devices 440, and the like.

Input device 415 may also include a touchscreen (e.g., resistive, surface acoustic wave, capacitive sensing, infrared, optical imaging, dispersive signal, or acoustic pulse recognition), keyboard (e.g., electronic keyboard or physical keyboard), buttons, switches, stylus, or combinations of these.

Display 404 may include dedicated LEDs for providing directing signals and feedback to a user.

Mass storage devices 440 may include flash and other nonvolatile solid-state storage or solid-state drive (SSD), such as a flash drive, flash memory, or USB flash drive. Other examples of mass storage include mass disk drives, floppy disks, magnetic disks, optical disks, magneto-optical disks, fixed disks, hard disks, CD-ROMs, recordable CDs, DVDs, recordable DVDs (e.g., DVD-R, DVD+R, DVD-RW, DVD+RW, HD-DVD, or Blu-ray Disc), battery-backed-up volatile memory, tape storage, reader, and other similar media, and combinations of these.

System 300 may also be used with computer systems having configurations that are different from computing device 315, e.g., with additional or fewer subsystems. For example, a computer system could include more than one processor (i.e., a multiprocessor system, which may permit parallel processing of information) or a system may include a cache memory. The computing device 315 shown in FIG. 4 is but an example of a computer system suitable for use. For example, in a specific implementation, computing device 315 is a wrist-mounted Biometric Analysis Device in communication with or incorporating the sensors of FIG. 3. Other configurations of subsystems suitable for use will be readily apparent to one of ordinary skill in the art. In other specific implementations, computing device 315 is a mobile communication device such as a smartphone or tablet computer. Some specific examples of smartphones include the Droid Incredible and Google Nexus One®, provided by HTC Corporation, the iPhone® or iPad®, both provided by Apple, BlackBerry Z10 provided by BlackBerry (formerly Research In Motion), and many others. The Biometric Analysis Device may be a laptop or a netbook. In another specific implementation, the Biometric Analysis Device is a non-portable computing device such as a desktop computer or workstation.

In an embodiment, system 300 may be incorporated into a single module. The module may have two electrodes on either side for measuring both heart rate and respiration. This module can be inserted into numerous types of wristband straps (leather, etc.) and form factors (such as key chain, steering wheel cover, etc.). The module, or the strap or other form factor, may also include a small OLED display to display the current time. The module may execute software that performs an embodiment of the method, thus eliminating the need for a clinician. Accordingly, the module may walk the user through steps to determine the user's resonance breathing frequency (or "calibrate" the user's resonance frequency) and provide feedback when the user's heart rate and respiration rate are in synchrony.

Figure 5:
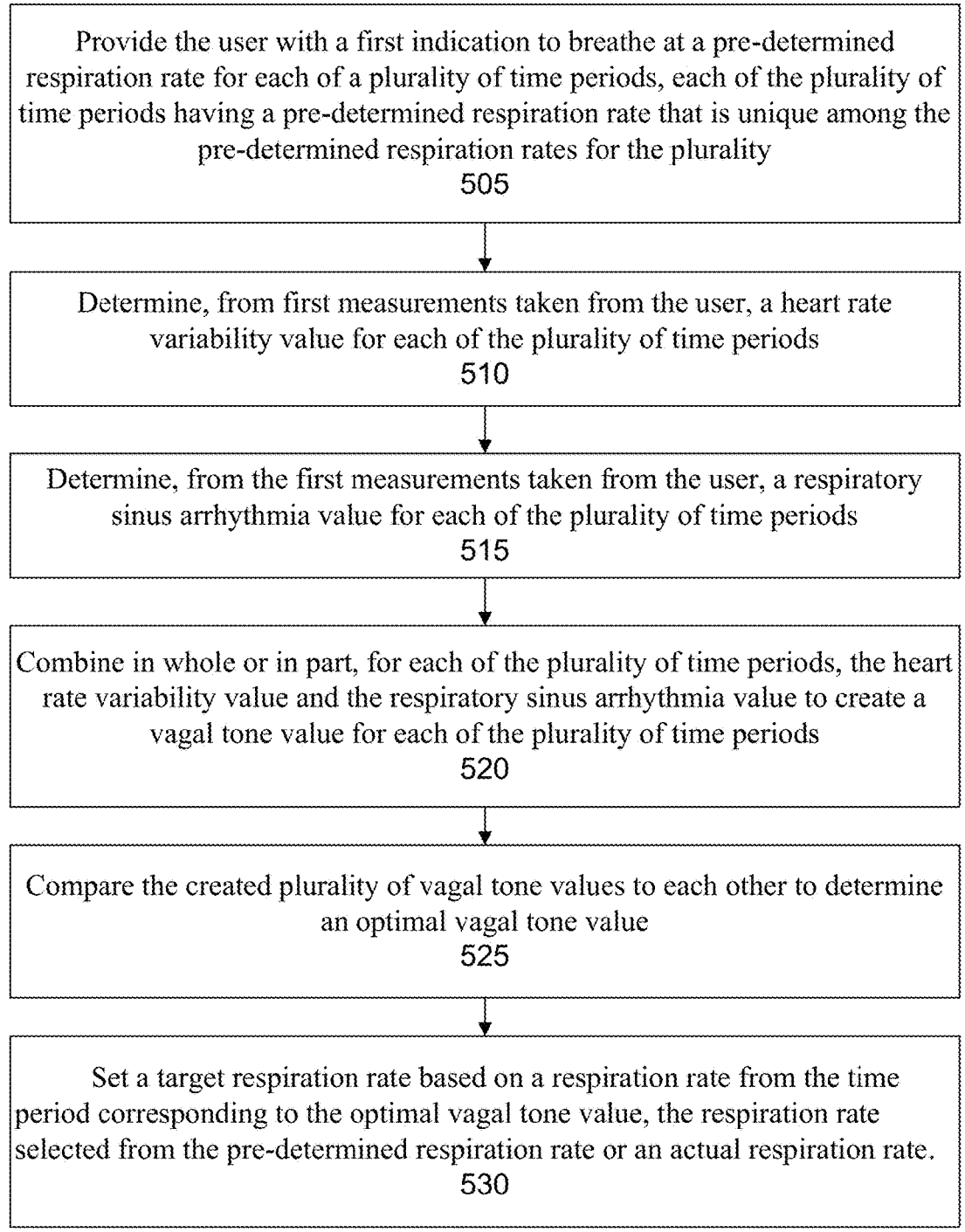
FIG. 5 is an exemplary block diagram of an embodiment of a method for determining a target breathing rate that is indicative of a person's resonance breathing frequency.

FIG. 5 is an exemplary block diagram of an embodiment of a method 500 for determining a target breathing rate that is indicative of the person's resonance breathing frequency, such that breathing at the target breathing rate improves the person's vagal tone. In an embodiment, after a user logs into a Biometric Analysis Device, attaches the appropriate sensors, and inputs the users gender, height, weight, and age, the Biometric Analysis Device may employ method 500 to provide the user with an optimal, target breathing rate. In method 500, in step 505, the user is provided with an indication to breathe at a pre-determined respiration rate for each of a plurality of periods, where each period has a pre-determined respiration rate that is unique among the pre-determined respiration rates for the plurality. In step 510, a HRV value is determined for each of the plurality of periods from measurements taken from the person. In step 515, a RSA value is determined for each of the plurality of periods from the measurements taken from the person. In step 520, from each of the periods, the HRV value and the RSA value from each of the periods are combined to create a vagal tone value for the respective period. In an embodiment, the vagal tone value is the result of a weighted combination of the HRV value and the RSA value where the weighting is 0.4 HRV value and 0.4 RSA value with the remaining 0.2 being supplied by Rate of Change (discussed within with regard to Equation 5). In step 525, the vagal tone values for each period are compared. From the period that produced the largest vagal tone value, the pre-determined respiration rate for that period is used to set a target respiration rate. In an embodiment, the target respiration rate is the pre-determined respiration rate for that period. In an embodiment, the target respiration rate is an actual, measured respiration rate from that period.

Figure 6:
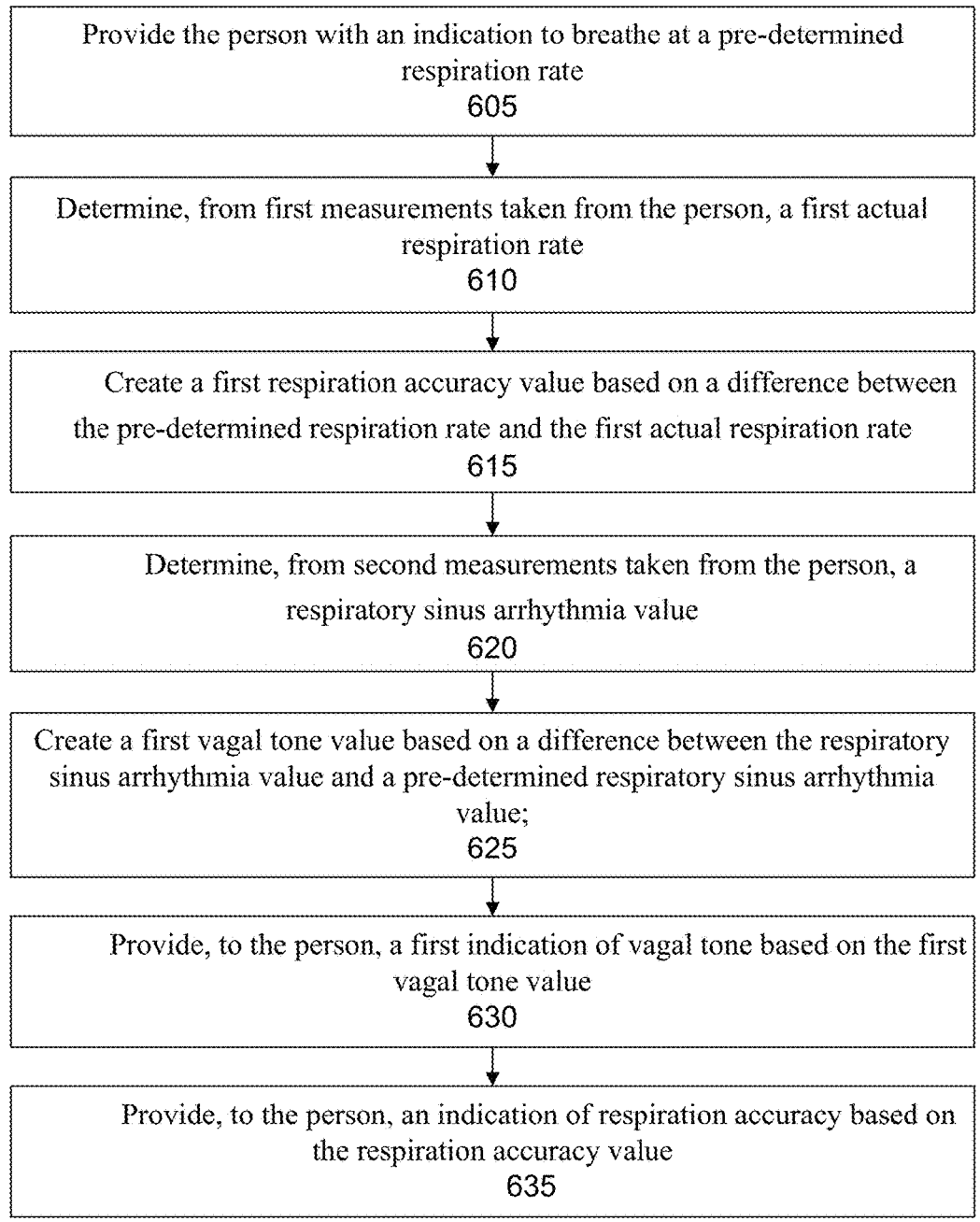
FIG. 6 is an exemplary block diagram of an embodiment of a method 600 for determining a vagal tone value indicative of a person's vagal tone.

FIG. 6 is an exemplary block diagram of an embodiment of a method 600 for determining a vagal tone value indicative of a person's vagal tone. In an embodiment, after a user logs into a Biometric Analysis Device, attaches the appropriate sensors, and inputs the user's gender, height, weight, and age, the Biometric Analysis Device may employ method 600 to determine a vagal tone value indicative of the user's vagal tone. In method 600, in step 605, a person is provided with an indication to breathe at a pre-determined respiration rate. In step 610, an actual respiration rate is determined from measurements taken from the user. In step 615, a respiration accuracy value is created based on a difference between the pre-determined respiration rate and the actual respiration rate. In step 620, an RSA value is determined from different measurements taken from the user. In an embodiment, the different measurements are of the person's heart rate, and in an embodiment, may be from an ECG. In step 625, a vagal tone value is created based on a difference between the RSA value and a pre-determined RSA value. In an embodiment, the pre-determined RSA value may be an estimated RSA value that is estimated based on knowledge of the person's physiology. In an embodiment, the predetermined RSA value may be from a prior determination of an RSA value for the person (i.e., a prior performance of step 620 on the person). In step 630, an indication of vagal tone is provided to the user based on the vagal tone value determined in step 625. In an embodiment, the indication of vagal tone is an indication of improved vagal tone when the vagal tone value is positive, which indicates an increase in the vagal tone value over the pre-determined vagal tone value. In step 635, an indication of respiration accuracy is provided to the user based on the respiration accuracy value.

Measurements and Calculations

Different biometrics are measured and the optimal measurement is stored for each measured biometric to calculate thresholds.

Heart Rate Variability (HRV)

In an embodiment, the HRV value is determined from the Peak Valley difference. That is, the HRV value is the calculated using the Peak Valley difference scaled to vary between values of 0 and 1. A heart rate sensor (which may provide a true ECG) is used to provide heart rate data. From such data a beat difference wave (also a wave may be referred to within as a "signal" or "data stream") is developed. The RMS value from the beat difference wave is used to calculate the Peak Valley difference. The Peak Valley difference is calculated using a moving average of the absolute value of the change in peak to peak heart beat over each new beat, according to Equation 1. This value is normalized to a 0-1 scale by using the maximum of a chosen constant and the best value a user has achieved. The optimal HRV value is 0. Peak Valley difference may be understood as the difference between a user's heart rate at the top of breath from the user's heart rate at the bottom of the breath. In other words, the difference between the number of beats per minute at the top of a user's breath and the number of beats per minute at the bottom of the breath. In an embodiment, the Peak Valley difference may be an ongoing estimation of the amplitude of the wave the user's heart produces. In other words, the amplitude of the sine wave created by the changes in the heart rate of an individual, where that "wave" is the user's heart rate plotted against time. Generally, any type of measure of Peak Valley difference is considered a measurement of HRV because it is a metric that highlights the variability of heart rate in an individual. RSA (discussed in more detail below) is based on the correlation between breathing and HRV. When in resonance both HRV and RSA will improve.

($HRV$ value):

$$PV_n = 1 - \frac{|v| + (p-1)PV_{n-1}}{p \cdot \max(k, best)} \qquad \text{Equation 1}$$

Where:
PV=the scaled Peak Valley difference (based on the RMS value from the beat difference wave) or "HRV value"
v=the new peak-to-peak heartbeat difference data point
p=a constant for the moving average. In an embodiment, p is 40.
k=a constant to scale the output.
best=the maximum value of adjusted PV previously achieved by the person.

Respiration

In an embodiment, a current respiration rate wave is calculated from data received from a respiration sensor.

Respiration Correlation with the Simulated Respiration Wave

The simulated respiration wave is based on the desired (or "directed") breathing rate. The Respiration Correlation value is a measure of how well the user is following the directed breathing rate. The Respiration Correlation value is calculated according to Equation 2, and runs between 0-1, with the optimal value being 0.

(Respiration Correlation value):

$$C_t = \cos\left(\frac{2t\pi}{b}\right) - r_t \qquad \text{Equation 2}$$

Where:
$C_t$=the correlation of the actual person's breathing rate to a target breathing rate, or "Respiration Correlation value"
t=the time increment
b=the target breathing speed of the individual
r=the respiration value taken at time t In Equation 2, the respiration value ("r") taken at time t is the peak adjusted respiration measurement, where "adjusted" means the data received from the respiration sensor is adjusted so that a complete inhalation results in a value of 1 and a complete exhalation results in a value of −1.

Respiratory Sinus Arrhythmia (RSA)

The RSA value is determined by Equation 3, below, which normalizes the respiration waveform and the beat difference wave so that they have the same output domain. This normalization process is based on the integral of the waveforms, which in an embodiment is estimated currently by a sine wave, but other methods for estimated are contemplated. The difference between the respiration wave and the beat difference wave is passed through a sigmoidal function. The output of this function shows the correlation between the waves and varies from 0 to 1, where 0 indicates there is no difference between the waves and 1 indicates the waves are antiparallel. RSA is a measurement of correlation between the respiration wave and beat difference wave. A good RSA value corresponds to a correlation that shows the two are in sync with each other, which happens when the user is breathing at their resonance breathing frequency.

In an embodiment, there are two waveforms: a first based on millisecond differences in heart beats, and a second based on respiration rate. Both are assumed to be sine waves. To normalize the ranges of these waves, the running average of the absolute value of each wave is taken. The calculus of this average gives the RMS of the wave, which is 2/π of the wave's maximum. This RMS value is also a reasonable estimate of the Peak Value difference for the heart rate data. If the running averages are divided by π/2 times the RMS result a normalized sin(x)-like graph with values that range from −1 to 1.

If the normalized respiration values are subtracted from the normalized heart rate values, it produces a correlation between the two waveforms, where 0 indicates there is no difference between the waves and 1 indicating that the waves are not at all correlated. The optimal value is 0.

($RSA$ value):

$$c = \frac{2}{\pi}\left(\frac{r_{n-1} - r_n}{r_{rms}} - \frac{h_{n-1} - h_n}{h_{rms}}\right) \qquad \text{Equation 3}$$

Where:
c=the correlation of heart rate to respiration, or "RSA value"
r=the stream of respiration data points
h=the stream of heart rate data points
rms values of r are calculated similarly to Peak Value difference of Equation 1
t=the time increment r=the respiration value taken at time t (as in Equation 2)

In an embodiment, the non-normalized respiration values may be run through a sigmoidal function to produce a correlation between the two waveforms ranging from 0 to 1.

Biometric Analysis (VT Score)

In an embodiment, a running score of the sum of weighted parameters is developed from the data continuously collected after the sensors have been attached to the user. This score represents one's overall level of vagal tone (which may be inversely related to stress) and is denoted as the "VT Score" within. It is calculated according to Equation 4, below. In an embodiment, the VT Score is based on solely the RSA value (see, e.g., FIG. 13). In another embodiment, the VT Score may be based on other individual parameters or groups of parameters. For example, the VT Score may be the weighted sum of the HRV value, the RSA value, and the Respiration Correlation value (see, e.g., FIG. 9). Respiration Correlation.

$$S_n = Ax + By + Cz \quad \text{Equation 4 (VT Score):}$$

Where:
A, B, and C=the values of the individual parameters, e.g., one or more of: HRV value, RSA value, and Respiration Correlation value.
x, y, and z=the weight given the associate parameter.

In an embodiment, a VT Score may be the sum of additional weighted parameters, e.g., $S_n=(Ax+By+Cz+Da+Eb+Fc)$, where D, E, and F are derived from measurements of additional user physiological conditions, e.g., user temperature, user galvanic skin response, and user blood pressure, and where a, b, and c are the weights chosen for the associated parameter. For example, the VT Score may include a correlation between galvanic skin response and a temperature response, since it has been determined that a simultaneous temperature increase and galvanic skin response decrease indicates strong parasympathetic improvement.

In an embodiment, biometric parameters that are weighted 0 may be measured in the background.

Rate of Change

In an embodiment, a Rate of Change for the VT Score is determined as well, and may be a factor in the VT Score itself, as shown using Equation 5, below. The rate at which a user's VT Score improves, which is an indication of the user transitioning from their sympathetic to parasympathetic nervous system (and activating their natural relaxation response), is an accurate representation of how good that user's vagal tone is.

In an embodiment, an optimal value of the Rate of Change (or "ROC") is determined during a calibration that determines a user's resonance breathing frequency. In the embodiment, ROC is continuously determined and weighted along with HRV and RSA during calibration. And, the optimal value of the Rate of Change is the highest recorded Rate of Change for the VT Score during the calibration. Thus, in an embodiment, to obtain a VT Score according to Equation 4 with ROC as one of the individual weighted parameters, the ROC (which is preferably high) must be manipulated so that the ROC goes to zero as it improves—which would then match the direction both RSA and HRV take when improving. Taking the reciprocal of the rate of change of the VT Score from one point to the next would supply a ROC value in which zero was the ideal score (e.g., (1/f(t)), where f(t) is the ROC of the VT Score).

In an embodiment, rather that manipulating ROC so that a decrease represents an improvement, both RSA and HRV are inverted so that an increase shows improvement, which then corresponds to the ROC showing improvement with an increase. For example, a $1-(1/f(t))$ conversion may be applied (where in this case f(t) is the RSA or HRV value), so that smaller values of RSA and HRV are converted to higher values, with a maximum of 1. Correspondingly, a VT Score calculated using such RSA, HRV, and ROC values would show improvement with an increase. The contributions of RSA, HRV, and ROC to a total VT Score may then be weighted as described within this application.

In an embodiment, the Rate of Change of the VT Score may be used to calculate the VT Score, as shown in the following equation:

(Rate of Change):

$$S_n = P_n + \left(\frac{P_n - P_0}{n}\right)k \quad \text{Equation 5}$$

Where:
$P_0$=the VT Score at time increment t=0 (typically the time increment immediately preceding n), before the rate of change is accounted for
$P_n$=the VT Score at time increment t=n, before the rate of change is accounted for
S=the final VT Score at time increment t=n.
k=a constant that weights how important Rate of Change is (e.g., previously at 0.2)

How quickly a user can improve their VT Score during a session is a parameter worth factoring into the VT Score itself, as shown in Equation 5, because a user that can quickly improve, e.g., their HRV value, or RSA value, generally has better vagal tone than someone who must take many times longer to do so. Thus, the Rate of Change may be a parameter that is summed in Equation 4 to arrive at the VT Score.

In an embodiment, a Rate of Change may be determined for individual parameters (e.g., RSA individually, or HRV individually). Similar to the ROC for the VT Score itself, a user that can quickly improve their HRV value or RSA value generally has better vagal tone than someone who must take longer to do so. Thus, a parameter-ROC contribution to the VT Score may be made based on the RSA or HRV individually. In addition, a Rate of Change may be based on a time between different threshold values.

Thresholds

Thresholds are developed or chosen from the biometric parameters calculated above. The thresholds can be adapted based on numerous factors, such as, for example, the change to respiration thresholds made at the various parts of the method disclosed in FIGS. 7 through 13, below. In embodiments, there may be specific thresholds with threshold ranges for each measured biometric, e.g., HRV value, RSA value, and Respiration Correlation. First, second, and third thresholds are determined for each biometric. The third threshold is greater than the optimal measurement, but the closest of the three to the optimal measurement.

Exemplary Thresholds, where A, B, and C of the VT Score are HRV value, RSA value, and Respiration Correlation value, respectively. The following thresholds have been determined empirically.

For A=HRV value
Threshold 3: 0.25
Threshold 2: 0.50
Threshold 1: 0.75
For B=RSA value Threshold 3: 0.25
Threshold 2: 0.50
Threshold 1: 0.75
For C=Respiration Correlation value
Threshold 3: 0.25 Respiration Correlation and smooth consistency
Threshold 2: 0.5 Respiration Correlation and smooth consistency
Threshold 2: 0.5 Respiration Correlation and erratic consistency
Threshold 1: 0.75 Respiration Correlation and smooth consistency
Threshold 1: 0.75 Respiration Correlation and erratic consistency In an embodiment, a "smooth" respiration consistency is indicated by a decreasing Respiration Correlation and an "erratic" respiration consistency is indicated by an increasing Respiration Correlation. The use of thresholds may be illustrated as follows with respect to the Respiration Correlation value. In an embodiment, the user is directed to breath at pre-determined rates (see, e.g., FIGS. 7 through 13), with the user's respiration rate being measured and a Respiration Correlation value being determined according to Equation 2. During the embodiment, so long as the Respiration Correlation value is below a determined first threshold for a determined duration, breathing is guided. When the Respiration Correlation value rises above the determined first threshold for a determined duration, a negative indicator is emitted. In the embodiment, to prevent the user from becoming annoyed, there is a minimum time gap between providing the user with a second negative indicator. And, after three negative indicators in a row, the minimum time gap changes to two times the original gap.

The use of thresholds may be further illustrated as follows with respect to the weights associated with the parameters of Equation 4. In this example, the VT Score is the sum of the weighted HRV value and RSA value. Thus, the respective weights of the HRV value and RSA value must sum to 1.0. In the following, "x"=the HRV value weight and "y"=the RSA value weight. The weights used to calculate the VT Score may change as follows:

1) If the HRV value is below threshold 2 and the RSA value is above threshold 2
   a. then x=1, y=0
2) If the HRV value is below threshold 2 and the RSA value is below threshold 2
   a. then x=0.5, y=0.5
3) If the HRV value is below threshold 3, and the RSA value is below threshold 1
   a. then x=0.5 and y=0.5
4) If the HRV value is below threshold 3 and the RSA value is below threshold 2
   a. then x=0.25 and y=0.75
5) If the HRV value is below threshold 3 and the RSA value is below threshold 3
   a. then x=0 and y=1

Thresholds may, in addition, have a time-based requirement. In the example above, a further requirement might be that the HRV value must have been below the HRV threshold 2 for a minimum of 1 minute, and then the HRV value must have also have gone below HRV threshold 3 before the RSA value is given the weight (y) of 1. In the example above, the thresholds determine the weights. In an embodiment, when the user is initially training, the thresholds determine the given weights. Then, once the user is experienced, RSA value is considered to be the most important value and is thus weighed more.

Feedback

In an embodiment, a Biometric Analysis Device implementing an embodiment of the method provides feedback to the user that is indicative of whether the user is, e.g., progressing toward an improved VT Score, not progressing toward an improved VT Score, breathing as directed, and not breathing as directed. Such feedback may be provided by user interfaces, such as audio, visual, and haptic interfaces. Such interfaces may also be used to guide the user in breathing at a pre-determined rate, e.g., during the determination of the user's specific resonance breathing frequency, and later in guiding (or training) the user to breathe at that specific resonance frequency. In an embodiment, the user is provided feedback using any or all of visual, audio, and haptic signals, such that the feedback may be considered "multispectral." In an embodiment, the directing signals provided by the Biometric Analysis Device may use any or all of visual, audio, and haptic signals, such that the directing signals may be considered "multispectral."

A haptic user interface involves a touching of the user. Most people have experienced a haptic interface in the form of the vibration that modern mobile phones use to indicate an incoming call, text, or email. In an embodiment, the negative indications discussed above in the illustration of the use of thresholds are delivered to the user by a haptic interface. The haptic interface is used by the Biometric Analysis Device to give the user one or two short, abrupt vibrations. In an embodiment, such indicators may be activated and deactivated through a double tap of Biometric Analysis Device electrodes.

In an embodiment, a visual interface includes one or more LED lights. In an embodiment, feedback is provided to the user using a rainbow light spectrum where red signifies the user is in a most-stressed state and the opposing end of the spectrum, purple, signifies the user is in a state of resonance (deep relaxation). In embodiments, the feedback may be based on the VT Score, or on individual parameter values, e.g., HRV value, or RSA value, or Respiration rate, or on combinations of values.

A User Experience

In an embodiment, a user experience begins with the user activating their Biometric Analysis Device, which begins measuring the user's biometric parameters. For a first-time user, the Biometric Analysis Device needs to be calibrated to that user. In other words, the Biometric Analysis Device is directed, by the user, to perform a calibration procedure in which the Biometric Analysis Device directs the user to breathe at pre-determined rates and, from the resulting data, the Biometric Analysis Device determines the user's resonance breathing rate.

Calibrating Resonance Breathing Frequency

In an embodiment, a user may play a game while their resonance breathing frequency is determined through adaptive intelligence. The game may be stopped at any time and all progress is saved up until the last fully measured breath rate checkpoint. In the game, breathing rates are cycled to determine which rate causes the most parasympathetic and vagal tone activity, as determined be, e.g., the breathing rate that produces the lowest VT Score, or lowest RSA value score. The breathing rate that produces the most vagal tone activity is saved for that user and is the specific resonance breathing frequency used in subsequent sessions with that user.

Tutorial

In the embodiment, the calibration may begin with a tutorial in which the user learns slow breathing techniques and how to prevent hyperventilation. During the tutorial, measurements are used to determine the Respiration Correlation value with feedback provided by a haptic interface. The calibration explains how to pace breathing without hyperventilating and what the "points" (see, e.g., step 720, FIG. 7) mean. The user is then guided through the following breath rates (13, 11, 9, 7 and 5 breaths per minute (b/m)). The user is directed to breathe at each rate until they receive a determined number of points in a row. Points are gained per breath or for a determined duration in which the Respiration Correlation value is between Respiration thresholds 1 and 2. During this part of the calibration, feedback, in the form of a negative (mindfulness) indicator is emitted when the Respiration Correlation value is above Respiration threshold 1 for longer than a determined duration. If the user receives a determined number of negative indicators consecutively a tutorial screen appears providing the user with instruction on how to breathe slowly without hyperventilating.

This process repeats with points accumulated for a determined number of breaths or determined duration of time the Respiration Correlation value is below its second threshold. Negative indicators are provided for breathing above threshold 2 for a determined number of breaths or longer than a determined amount of time.

This process is again repeated, but with points for breaths below Respiration threshold 3 and negative indicators provided when above threshold 3.

General Resonance Frequency Calibration

The actual calibration (or "determination") of the user's resonance breathing frequency begins after the tutorial. In this main phase of the calibration, the user is directed to breathe (while measurements are taken continuously) at rates that are cycled to determine which breathing rate activates the parasympathetic response the soonest, causes the greatest sympathetic to parasympathetic improvement, and brings the current RMS and RSA values closest to optimal.

The running VT Score (Equation 4) is calculated during this phase of the calibration game. Also, the Biometric Analysis Device indicates when to inhale and exhale at different breathing rates with half-second differences. The user completes a full breath rate measurement after a determined number of points in a row, where points are gained per breath or for a determined duration during which the Respiration Correlation value is below its third threshold. A negative indicator is provided when the Respiration Correlation is above threshold 3 for a determined number of breaths or a determined duration. In the embodiment, the points go to 0 if a negative indicator is provided. Positive indicators are provided when points are attained.

In this general phase, directed breathing rates include: 7 b/m, 6 b/m, and 5 b/m. The user is directed to breathe at these rates for determined durations while the VT Score is calculated. During this phase, the VT Score is calculated with the HRV value weighted highest. In an embodiment in which GSR and temperature are being measured and contribute to the VT Score, the VT Score is calculated with the HRV value weighed highest until a threshold is reached, then GSR and Temperature measurements are weighted higher that the HRV value.

After the user has completed breathing at the 7, 6, and 5 b/m, further precision is to be gained by directing the user to breathe at rates that are half a breath per minute above and below the rate that produced the best VT Score. For example, if 5 b/m produced the lowest VT Score then the user is directed to breathe at both 5.5 b/m and 4.5 b/m, with continuous measuring. The directed breathing rate that produced the lowest VT Score is then set as the user's general resonance breathing frequency. Generally, breathing rates may be repeated to ensure there wasn't a measurement error.

In an embodiment of the general phase, a different game format may be used for each directed breathing rate. In an embodiment, the Biometric Analysis Device displays simple breathing technique reminders. In an embodiment, a warm up period precedes the beginning of each breath rate for a determined amount of time.

Training

After the general phase is used to produce the user's general resonance breathing frequency, the Biometric Analysis Device may be used to train the user to breathe at that breathing frequency. In an embodiment, a user is trained at their general resonance frequency for a determined minimum number of full sessions, where a successful full session is defined as a session during which the Respiration Correlation value remained above a determined threshold for a determined duration.

An embodiment of a training session includes three stages: Initial Biometric Measurement and Immediate Feedback; Sympathetic to Parasympathetic Improvement; and Maintain Parasympathetic State. In stage 1, Initial Biometric Measurement and Immediate Feedback, a user attach the Biometric Analysis Device, which begins measurements and providing immediate feedback. In an embodiment, the Biometric Analysis Device is activated when users make contact with electrodes on the device, with a contact allowing a threshold current to be conducted between the electrodes. The Biometric Analysis Device then provides feedback through colors of the spectrum that correspond to their calculated RSA value.

In stage 2, Sympathetic to Parasympathetic Improvement, the goal is for the user to improve their RSA value by breathing at the directed frequency, with improvements in RSA value being shown by the color of light transitioning from the red end of the spectrum toward the purple end. Preferentially, the user is able to achieve an RSA value that results in the Biometric Analysis Device displaying a purple color, which indicates the user has reached the RSA value that the user attained during their most recent calibration phase.

In state 3, Maintain Parasympathetic State, the tracked parameter values from Stage 2 are analyzed. Rates of change are determined for the VT Score and each parameter for the session. For rates of change, the VT Score or value used is the lowest that was maintained for a pre-determined time during the session. If the VT Score or parameter value reached a new low during the session, it is stored as the new goal for the VT Score or particular parameter. In addition, the rate at which the user went from a high sympathetic state to parasympathetic state is stored for future reference. Time within thresholds are measured and recorded as well for each session.

In a training session, feedback may be provided by both haptic, LED, and audio interfaces. A questionnaire may appear if the user receives a pre-determined number of negative indicators during the session, with the questionnaire being used to determine whether the user is hyperventilating. The Biometric Analysis Device displays technique recommendations to prevent hyperventilation if the user's responses indicating they are hyperventilating.

Specific Resonance Frequency Calibration

After the user completes a minimum number of full sessions at their general resonance breathing frequency, a specific phase of calibration may be entered. The specific phase is directed to producing a more specific resonance breathing frequency. In the specific phase, the user completes a determined number of full sessions at the general resonance breathing frequency to determine whether there is a "trend"—the trend showing either: 1) the user's heart rate increases before inhalation or 2) the user begins an inhalation before their heart rate increases.

If a trend shows heart rate increasing before inhalation then the user's resonance breathing frequency will need to be increased slightly. Therefore, the next set of directed breathing rates may start at 0.3 breaths per minute over the user's general resonance breathing frequency and decrease by increments of 0.1 for five iterations. Or, the next set of directed breathing rates may start at the user's general resonance breathing frequency and increase by increments of 0.1 for five iterations.

If a trend shows inhalation beginning before heart rate starts increasing then the user's resonance breathing frequency will need to be decreased slightly. Therefore, the next set of breath rates may start 0.3 breaths per minute below the user's general resonance breathing frequency and increase by increments of 0.1 for five iterations. Or, the next set of directed breathing rates may start at the user's general resonance breathing frequency and decrease by increments of 0.1 for five iterations.

If there is a "trend," the resulting increase or decrease is made and the directed breathing rates cycled through while the VT Score is calculated. If there is no "trend," then no further breathing need be directed in this phase.

Generally, in this phase, in an embodiment based on RSA and HRV values, the RSA value component of the VT Score should be weighted more than the HRV value when the user is pacing correctly—as determined by the Respiration Correlation value. In an embodiment in which GSR and temperature are also being measured and contribute to the VT Score, the RSA value component of the VT Score should be weighted more than the HRV, GSR, and Temp values when the user is pacing correctly. As discussed above, in an embodiment, a Rate of Change of the VT Score may be a weighted component of the VT Score. And, in an embodiment, a Rate of Change of any individual parameter (e.g., RSA and HRV) may be a weighted component of the VT Score.

As before, for each directed breathing rate, the user completes a full breath rate measurement after receiving a determined number of points in a row. In this phase, points are gained per breath or for breathing for a duration during which the Respiration Correlation value is below its third threshold. A negative indicator is provided when above threshold 3 for a determined number of breaths or a determined duration, and the points go to 0 if a negative indicator is emitted. Feedback may be provided by both haptic and LED interfaces. Positive indicators are emitted when points are attained. And the directed breathing rate that produced the lowest running score (best RSA) is stored.

Further Training

The longer a user trains with the Biometric Analysis Device the more accurate their resonance breathing frequency becomes. After the user completes a pre-determined number of full sessions at their specific resonance breathing frequency, the user may enter a phase in which the effect of an added pause to the specific resonance breathing frequency on the RSA value is determined.

The pause (or "hold") is part of breath as follows: the sum of inhale time, inhale hold, exhale time, and exhale hold equal 100% of the period of the breath. Keeping the period of the breath fixed, the user may be directed by the Biometric Analysis Device to insert a hold after each inhalation and exhalation. The duration of each hold may begin at, e.g., 1 second. The RSA value is calculated with a full breath rate measurement requiring the user receive a determined number of points in a row. Subsequently, the duration of the hold is decreased by 0.1 second and a full breath rate measurement performed. The process is repeated until the hold become zero. From the calculated RSA values for each breath rate measurement, the pause associated with the lowest RSA value is used to update the specific resonance breathing rate to contain that optimal pause.

Additional Optional Feedback Methods

In an embodiment, when a parameter or VT Score is below a given threshold, one or more positive indicators may be emitted. Similarly, when a parameter or VT Score is above a given threshold, one or more negative indicators may be emitted.

In an embodiment, all biometric data may be recorded, displayed in graphs on the Biometric Analysis Device, and presented in a portal for doctors and patients.

In an embodiment, a positive indicator may be emitted if a current parameter measurement or VT Score is increased from a previous value.

In an embodiment, breathing may be guided while the user is receiving feedback on breathing and feedback on the user's resonance state (e.g., where the user is with regard to particular thresholds). In the embodiment, the breathing guide is stopped after the user's respiration value goes below the third threshold. In an embodiment, if the user does not wish to see LEDs, but still wishes feedback, the user may select to have feedback solely through vibrations. In an embodiment, the breathing guide is stopped when either the RSA value or respiration value is below the third threshold. In the embodiment, if the user does not wish to their breathing guided, but still wish to receive breathing feedback, then the user may select to have breathing feedback provided through vibrations, e.g., a soothing vibration may be provided when the user is below the third threshold, or in a resonance state such that their RSA is below the third threshold. In an embodiment, the user may receive as feedback a series of three short vibrations to indicate that the user's RSA value is rising above the first threshold, or when the user's respiration value is rising above the second threshold.

Other Possible Indicators:
Extra Positive Indicator
Visual—green light
Haptic—long, massaging vibration
Auditory—long sound waves
low pitch tone if feedback is being based on compared intervals (the current interval is compared to the previous interval), which is described in U.S. application Ser. No. 15/428,115, and which is incorporated by reference.
Positive Indicator
Visual—blue or yellow light
Haptic—short, massaging vibration
Auditory—medium sound waves if feedback is being based on thresholds as described earlier under "Thresholds," paragraphs 80-88.
medium pitch Tone if feedback is being based on compared intervals instead of thresholds.
Negative Indicator
Visual—red light
Haptic—one or two short, abrupt vibrations
Auditory—short sound waves if feedback is being based on thresholds.

high pitch if feedback is being based on compared intervals.

Breathing Guide

Visual—lights slowly changing colors

Haptic—Subtle and Soothing Guided Exhale

Auditory—changing tone

In an embodiment, a guide for Directed Breathing is haptic, with the Biometric Feedback Device delivering a vibration on exhale, with the vibration decreasing in force as the user exhales.

Figure 7:
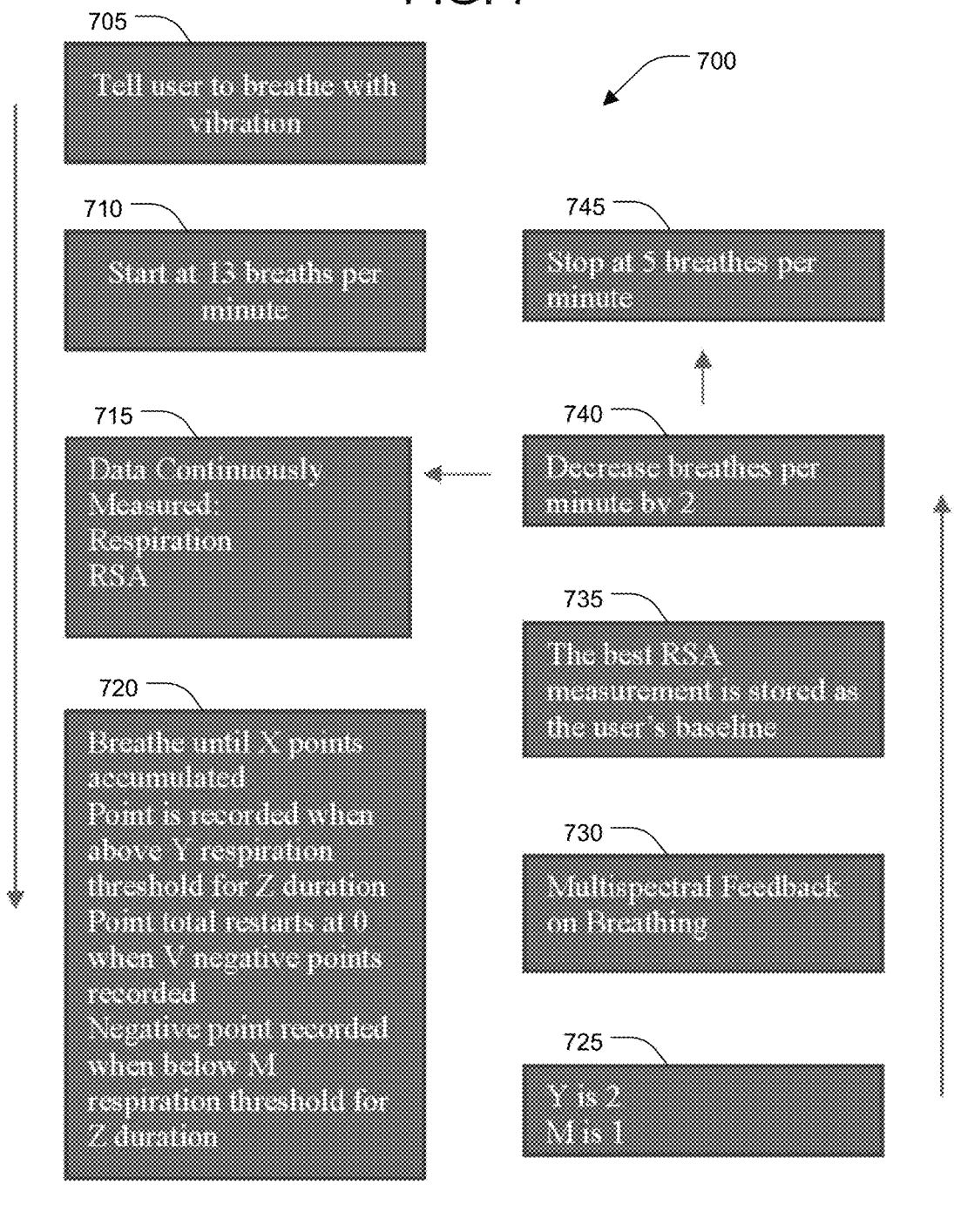
FIG. 7 shows a block diagram illustrating a first part of an embodiment of a method for providing a user with a breathing rate that is calibrated to the user's resonance breathing frequency.

FIGS. 7 through 13 show block diagrams illustrating an embodiment of a method for providing a user with a breathing rate that is calibrated to the user's resonance breathing frequency. FIG. 7 shows a first method part 700 of the method for providing a user with a breathing rate calibrated to the user's resonance frequency. First method part 700 is generally directed to teaching the user how to breathe at a directed rate. In step 705, the user is directed to breathe with an indicating vibration. In step 710, the user is directed to breathe at 13 breaths per minute (b/m). In step 715 and until breathing is stopped at step 745, the user's respiration rate and heart rate are continuously measured to develop associated Respiration Correlation values (according to Equation 2) and RSA values (according to Equation 3). In step 720, the user is directed to breathe until X points are accumulated. Points are accumulated when the user is respiring with a Respiration Correlation value above a Y respiration threshold for a duration Z, with a point being accumulated each duration Z. The point total returns to 0 when V negative points are recorded, where negative points are recorded when the user's Respiration Correlation value is below an M respiration threshold for a Z duration. In step 725 it is noted that for method part 700 of the method, the Y respiration threshold is 2 and the M respiration threshold is 1. In step 730 it is noted that during method part 700 of the method, the user is provided multispectral feedback based on the Respiration Correlation to help the user achieve the directed breathing rate. In step 735, the best (i.e., lowest) RSA value recorded at the directed breathing rate is stored as the user's baseline. In step 740, the directed breathing rate is decreased by 2 breaths per minute and steps 715 through 740 repeated until data is collected on the user breathing at 5 breaths per minute and, at step 745, first method part 700 is ended.

Figure 8:
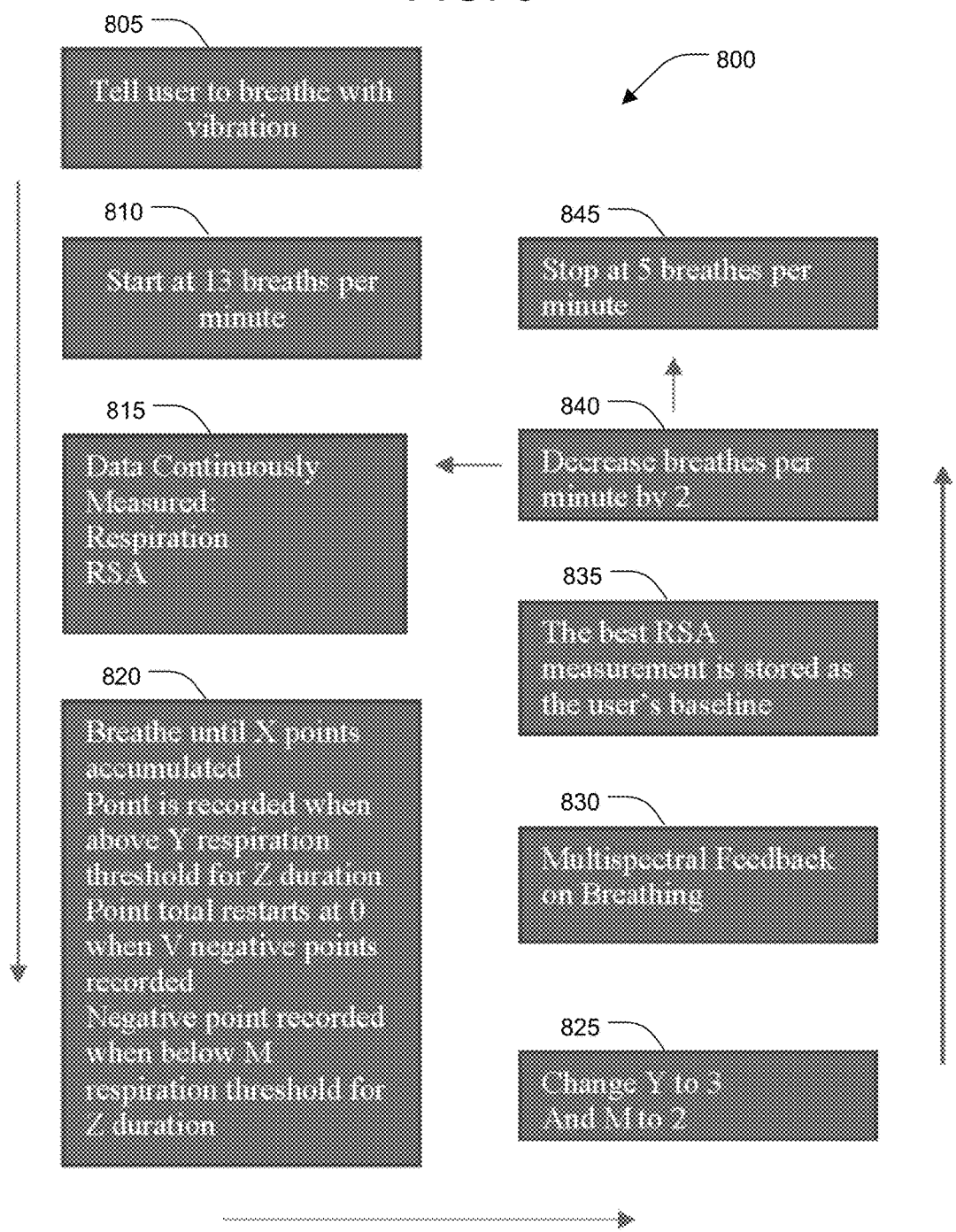
FIG. 8 shows a block diagram illustrating a second part of the embodiment of FIG. 7 for providing a user with a breathing rate that is calibrated to the user's resonance breathing frequency.

FIG. 8 shows a second method part 800 of the method for providing a user with a breathing rate calibrated to the user's resonance breathing frequency. Second method part 800 is generally directed to teaching the user how to breathe at a directed rate, with the change being that Y is changed to 3 and M is changed to 2. In step 805, the user is directed to breathe with an indicating vibration. In step 710, the user is directed to breathe at 13 breaths per minute (b/m). In step 815 and until breathing is stopped at step 845, the user's respiration rate and heart rate are continuously measured to develop associated Respiration Correlation values and RSA values, using Equation 2 and Equation 3, respectively. In step 820, the user is directed to breathe until X points are accumulated as discussed previously. In step 825 it is noted that for method part 800 of the method, points are accumulated based on a Y respiration threshold of 3 and an M respiration threshold of 2. In step 830 it is noted that during method part 800 of the method, the user is provided multispectral feedback based on the Respiration Correlation to help the user achieve the directed breathing rate. In step 835, the best (i.e., lowest) RSA value recorded (during any step of method parts 700 or 800) at the directed breathing rate is stored as the user's baseline. In step 840, the directed breathing rate is decreased by 2 breaths per minute and steps 815 through 840 repeated until data is collected on the user breathing at 5 breaths per minute and, at step 845, second method part 800 is ended.

Figure 9:
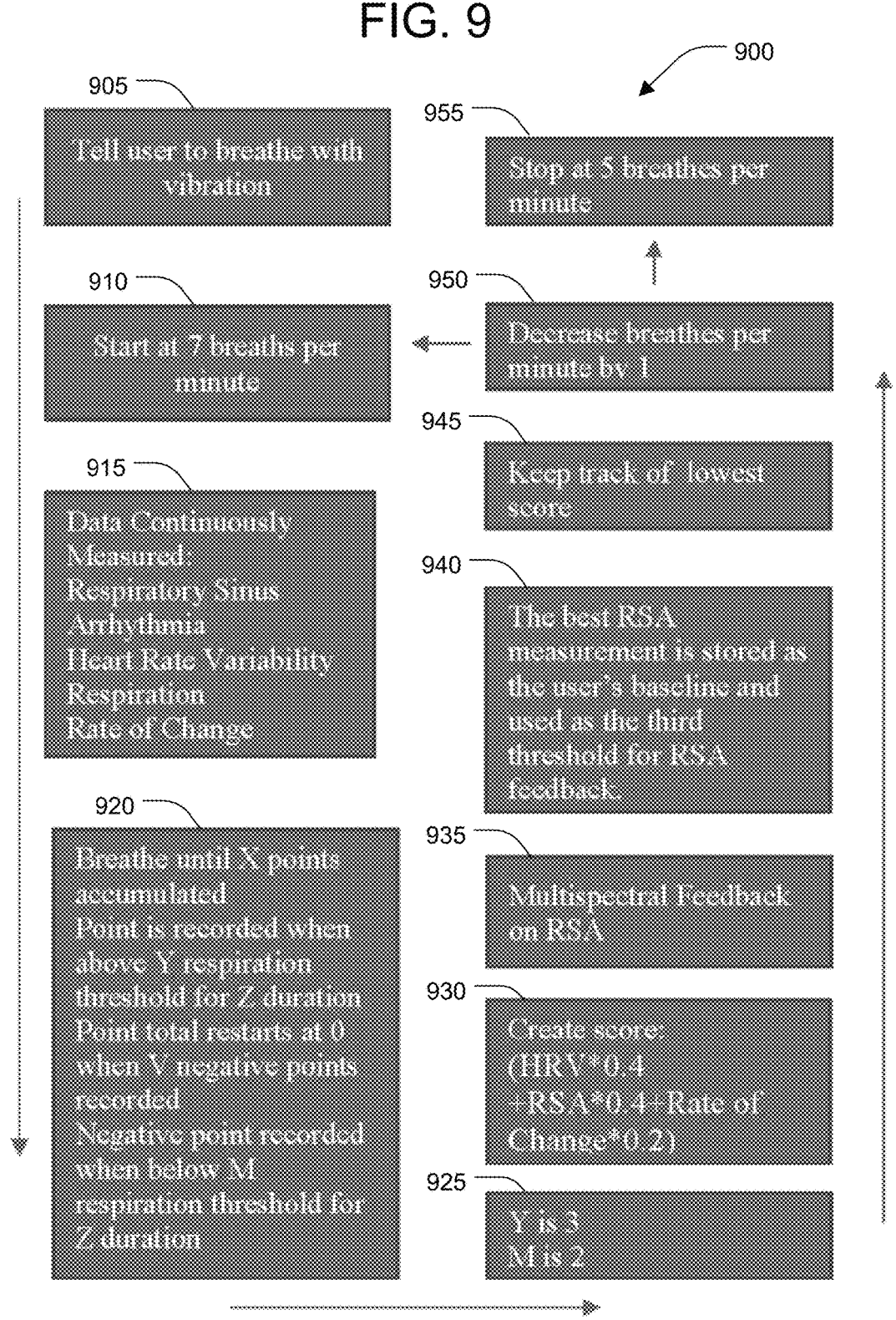
FIG. 9 shows a block diagram illustrating a third part of the embodiment of FIG. 7 for providing a user with a breathing rate that is calibrated to the user's resonance breathing frequency.

FIG. 9 shows a third method part 900 of the method for providing a user with a breathing rate calibrated to the user's resonance frequency. Third method part 900 is generally directed to determining the user's resonance breathing frequency. In step 905, the user is directed to breathe with an indicating vibration. In step 910, the user is directed to breathe at 7 breaths per minute (b/m), where 7 breaths per minute has been chosen as a starting point because it has been determined to be above the resonance breathing frequency for the vast majority of people. In step 915 and until breathing is stopped at step 845, the user's respiration rate and heart rate are continuously the user's respiration rate and heart rate are continuously measured to develop associated Respiration Correlation values, RSA values, HRV values (according to Equation 1), and Rate of Change values (according to Equation 5). In step 920, the user is directed to breathe until X points are accumulated, as discussed previously. In step 925 it is noted that for method part 900 of the method, points are accumulated based on a Y respiration threshold of 3 and an M respiration threshold of 2. In step 930, after X points are accumulated, a VT Score is created based on Equation 4, where in this embodiment, A is HRV, B is RSA, and C is Rate of Change: HRV*0.4+RSA*0.4+Rate of Change*0.2, with the weights in this embodiment being 0.4, 0.4, and 0.2, respectively. In step 930 (as in step 915), the HRV value is calculated according to Equation 1, the RSA value is calculated according to Equation 3, and the Rate of Change value is calculated according to Equation 5. In step 935, it is noted that during method part 900, the user is provided multispectral feedback based on the RSA value to help the user achieve the directed breathing rate. In step 940, the best (i.e., lowest) RSA value recorded (during any step of method part 900) is stored as the user's baseline RSA and as the third threshold for RSA feedback (as discussed earlier, the direction to breathe is given to the user so long as the Respiration Correlation value is lower than the third threshold. In step 945, the lowest VT Score (from the multiple iterations of step 930) is tracked and stored. In step 950, the directed breathing rate is decreased by 1 breath per minute and steps 910 through 950 repeated until data is collected on the user breathing at 5 breaths per minute and, at step 955, third method part 900 is ended.

Figure 10:
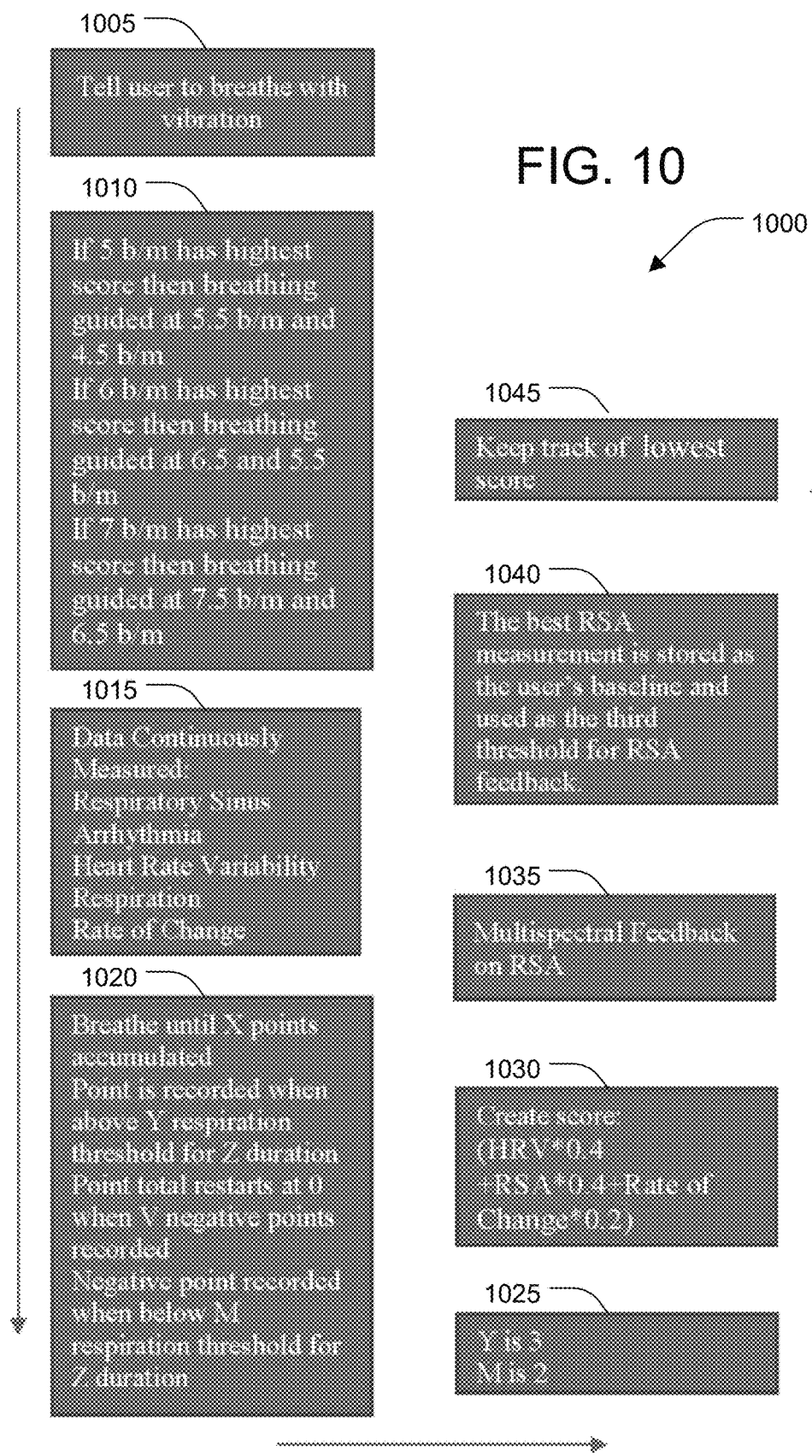
FIG. 10 shows a block diagram illustrating a fourth part of the embodiment of FIG. 7 for providing a user with a breathing rate that is calibrated to the user's resonance breathing frequency.

FIG. 10 shows a fourth method part 1000 of the method for providing a user with a breathing rate calibrated to the user's resonance breathing frequency. Fourth method part 1000 is generally directed to determining the user's best RSA value based on the lowest VT Score determined in step 945 and the breathing rate associated with that lowest VT Score. In step 1005, the user is directed to breathe with an indicating vibration. In step 1010, the directed breaths per minute corresponding to the lowest stored VT Score (from step 945) is determined. The breath per minute value determined from step 945 is bracketed by adding and subtracting half a breath per minute to create two new breath per minute values, and the user is directed to perform steps 1015 through 1040 at each new value. For example, if data from step 945 indicates that 5 breaths per minute produced the lowest VT Score, then steps 1015 through 1040 are performed twice, with the user first being directed to breath at 5.5 b/m and then being directed to breathe at 4.5 b/m. In step 1015 and until breathing is stopped at step 1045, the user's respiration rate and heart rate are continuously measured to develop the Respiration Correlation, RSA, HRV, and Rate of Change values, as discussed with reference to step 915. In step 1020, the user is directed to breathe until X points are accumulated, as discussed previously. In step 1025 it is noted that for method part 1000 of the method, points are accumulated based on a Y respiration threshold of 3 and an M respiration threshold of 2. In step 1030, after X points are accumulated, a VT Score is created based on the equation: HRV*0.4+RSA*0.4+Rate of Change*0.2, as discussed regarding step 930. In step 1035, it is noted that during method part 1000 of the method, the user is provided multispectral feedback based on the RSA value to help the user achieve the directed breathing rate. In step 1040, the best (i.e., lowest) RSA value recorded (during any step of method parts 900 or 1000) is stored as the user's baseline RSA and as the third threshold for RSA feedback. The directed respiration rate associated with the best RSA value recorded is considered to be the calibrated general resonance breathing frequency. In step 1045, the lowest VT Score from fourth method part 1000 is stored and fourth method part 1000 ends.

Figure 11:
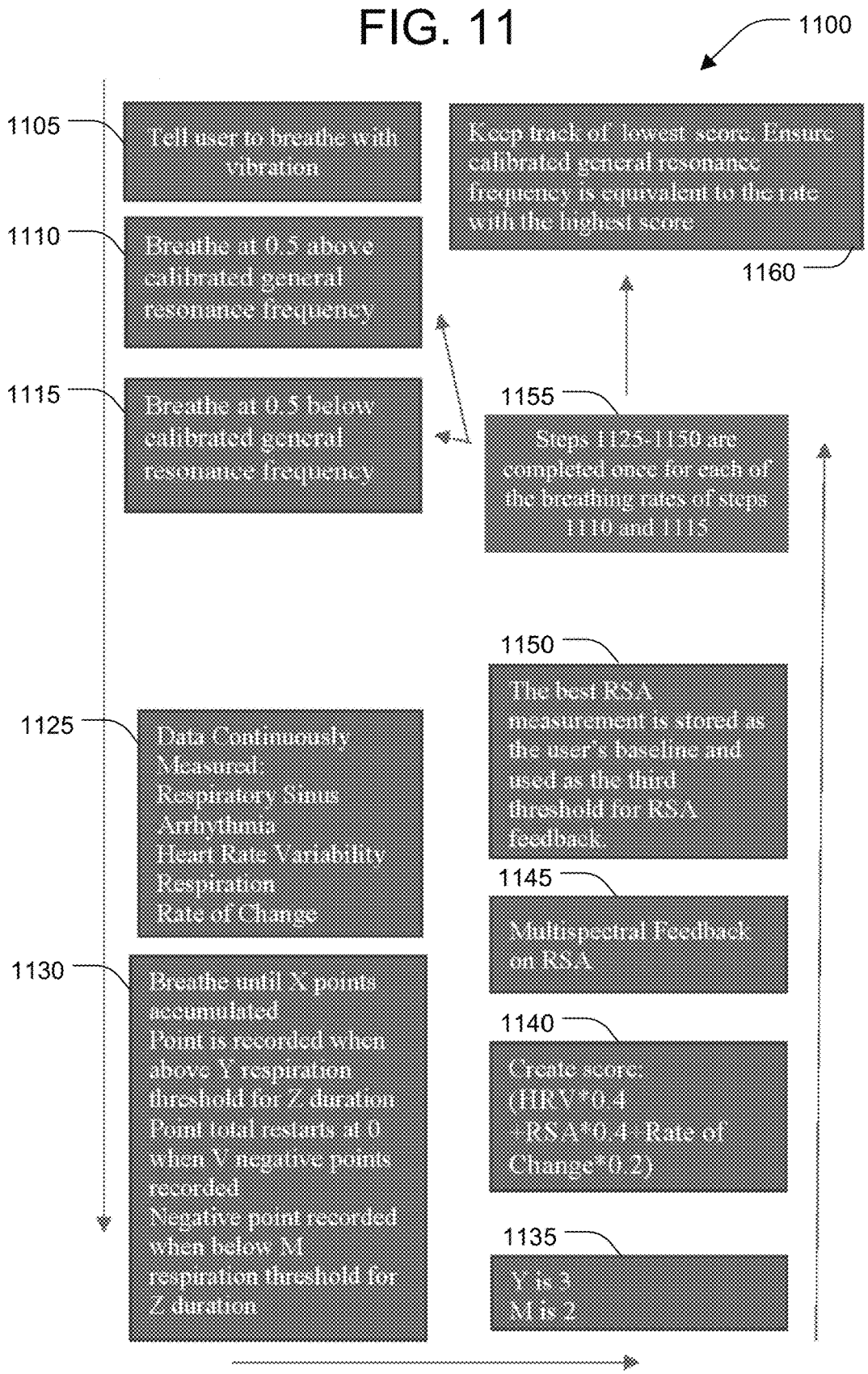
FIG. 11 shows a block diagram illustrating a fifth part of the embodiment of FIG. 7 for providing a user with a breathing rate that is calibrated to the user's resonance breathing frequency.

FIG. 11 shows a fifth method part 1100 of the method for providing a user with a breathing rate calibrated to the user's resonance breathing frequency. Fifth method part 1100 is generally directed to improving on the determination of the user's best RSA value from step 1040 and the breathing rate associated with that lowest RSA value. In step 1105, the user is directed to breathe with an indicating vibration. In step 1110, the user is directed to breathe at 0.5 b/m above the breathing rate associated with the lowest recorded RSA value from step 1040. That increased breathing rate is then used during steps 1125 through 1150. In step 1125, the user's respiration rate and heart rate are continuously measured to develop the Respiration Correlation, RSA, HRV, and Rate of Change values, as discussed with reference to step 915. In step 1130, the user is directed to breathe until X points are accumulated, as discussed previously. In step 1135 it is noted that for method part 1100 of the method, points are accumulated based on a Y respiration threshold of 3 and an M respiration threshold of 2. In step 1040, after X points are accumulated, a VT Score is created based on the equation: HRV*0.4+RSA*0.4+Rate of Change*0.2, as discussed with regard to step 930. In step 1145, it is noted that during method part 1100 of the method, the user is provided multispectral feedback based on the RSA value to help the user achieve the directed breathing rate. In step 1050, the best (i.e., lowest) RSA value recorded (during any step of method part 900, method part 1000, or method part 1100) is stored as the user's baseline RSA and as the third threshold for RSA feedback. The directed respiration rate associated with the best RSA value recorded is considered to be the calibrated general resonance breathing frequency. Method part 1100 then goes to step 1115. In step 1115, the user is directed to breathe at 0.5 b/m below the breathing rate associated with the lowest recorded RSA value from step 1040. That decreased breathing rate is then used during steps 1125 through 1150 as just discussed. Step 1155 indicates that each of the breathing rates of steps 1110 and 1115 are used for an iteration through the process of steps 1125 to 1150. In step 1160, the lowest VT Score from fifth method part 1100 is stored. Also, in step 1160, the breathing rate associated with the lowest VT Score from method part 1100 is determined to be the user's specific resonance breathing frequency. In an embodiment, the method is checked by comparing the VT Score from method part 1100 to the VT Scores from previous method parts—when the VT Score from method part 1100 is the lowest, the method is determined to be functioning correctly.

Figure 12:
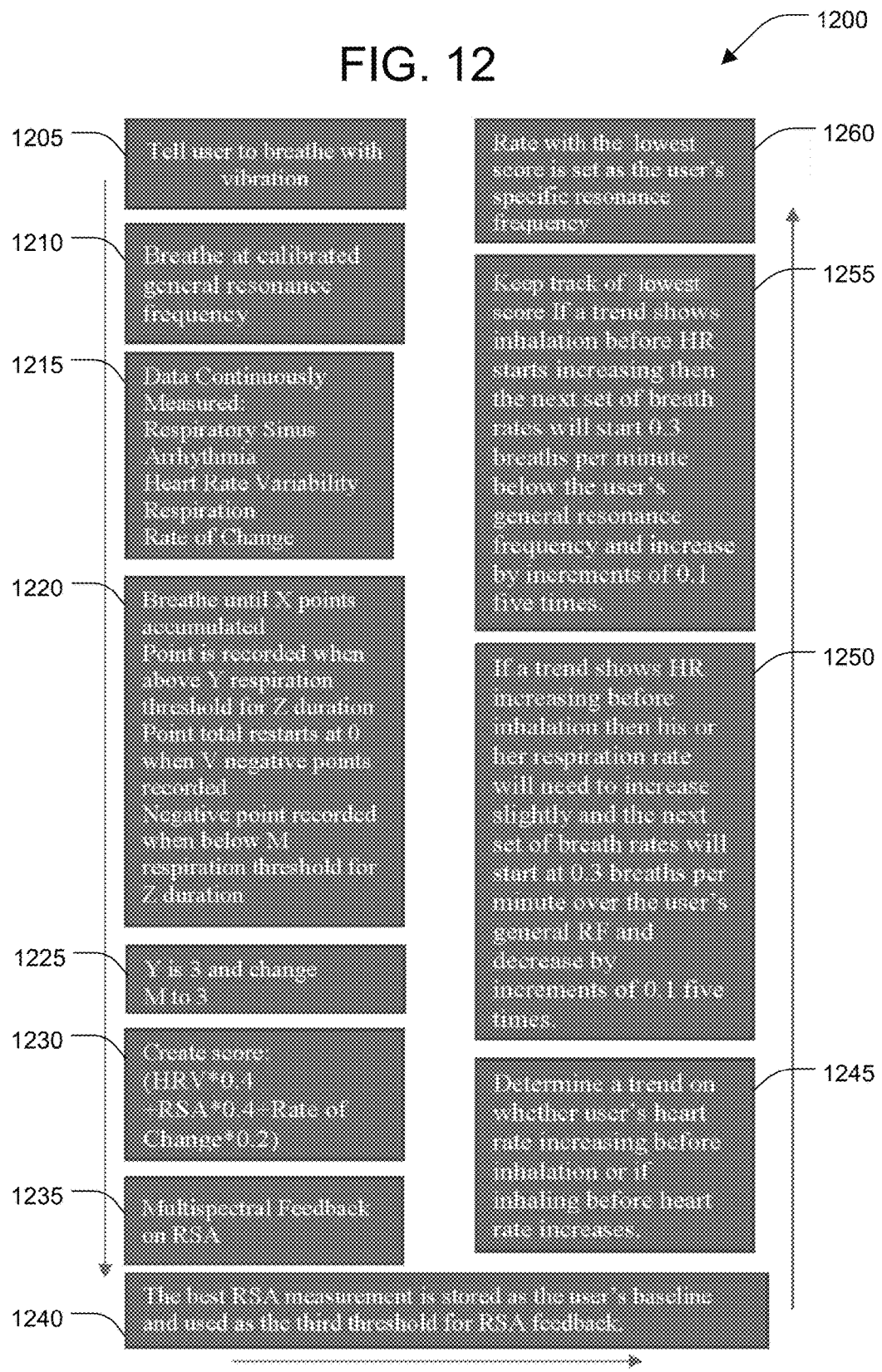
FIG. 12 shows a block diagram illustrating a sixth part of the embodiment of FIG. 7 for providing a user with a breathing rate that is calibrated to the user's resonance breathing frequency.

FIG. 12 shows a sixth method part 1200 of the method for providing a user with a breathing rate calibrated to the user's resonance frequency. Sixth method part 1200 is generally directed to improving the precision of the determination of the user's best (i.e., lowest) RSA value from step 1150 and the breathing rate associated with that lowest VT Score value from step 1160. In step 1205, the user is directed to breathe with an indicating vibration. In step 1210, the user is directed to breathe at the breathing rate associated with the lowest recorded RSA value from step 1150. In step 1215, the user's respiration rate and heart rate are continuously measured to develop the Respiration Correlation, RSA, HRV, and Rate of Change values, as discussed with reference to step 915. In step 1220, the user is directed to breathe until X points are accumulated, as discussed previously. In step 1225 it is noted that for method part 1200 of the method, points are accumulated based on a Y respiration threshold of 3 and an M respiration threshold of 3. In step 1230, after X points are accumulated, a VT Score is created based on the equation: HRV*0.4+RSA*0.4+Rate of Change*0.2, as discussed with regard to step 930. In step 1235, it is noted that during method part 1200 of the method, the user is provided multispectral feedback based on the RSA value to help the user achieve the directed breathing rate. In step 1240, the best (i.e., lowest) RSA value recorded (during any step of method parts 900, 1000, 1100, or 1200) is stored as the user's baseline RSA and as the third threshold for RSA feedback. The directed respiration rate associated with the best RSA value recorded is considered to be the calibrated general resonance breathing frequency. In step 1245, it is determined from the respiration and heart rate measurements from step 1215 whether there is a trend that shows the user's heart rate increasing before inhalation begins or if the user begins inhaling before their heart rate increases. If a trend shows the user's heart rate increasing before inhalation begins, then, in step 1250, the user's respiration rate will need to be increased slightly. The next set of directed breathing rates will start at 0.3 breaths per minute over the user's calibrated general resonance breathing frequency and decrease by increments of 0.1 b/m for five iterations of steps 1215 through 1240. During these iterations, the lowest VT Score and associated directed breathing rate are stored as before. Returning to step 1245, if a trend shows inhalation begin before the user's heart rate increases, then, in step 1255, the user's respiration rate will need to be decreased slightly. The next set of directed breathing rates will start at 0.3 breaths per minute below the user's calibrated general resonance breathing frequency and increase by increments of 0.1 b/m for five iterations of steps 1215 through 1240. During these iterations, the lowest VT Score and associated directed breathing rate are stored as before. After steps 1250, or 1255, or if no trend is found in step 1245, then, in step 1260, the directed breathing rate associated with the lowest VT Score is determined to be the user's specific resonance breathing frequency and sixth method part 1200 ends.

Figure 13:
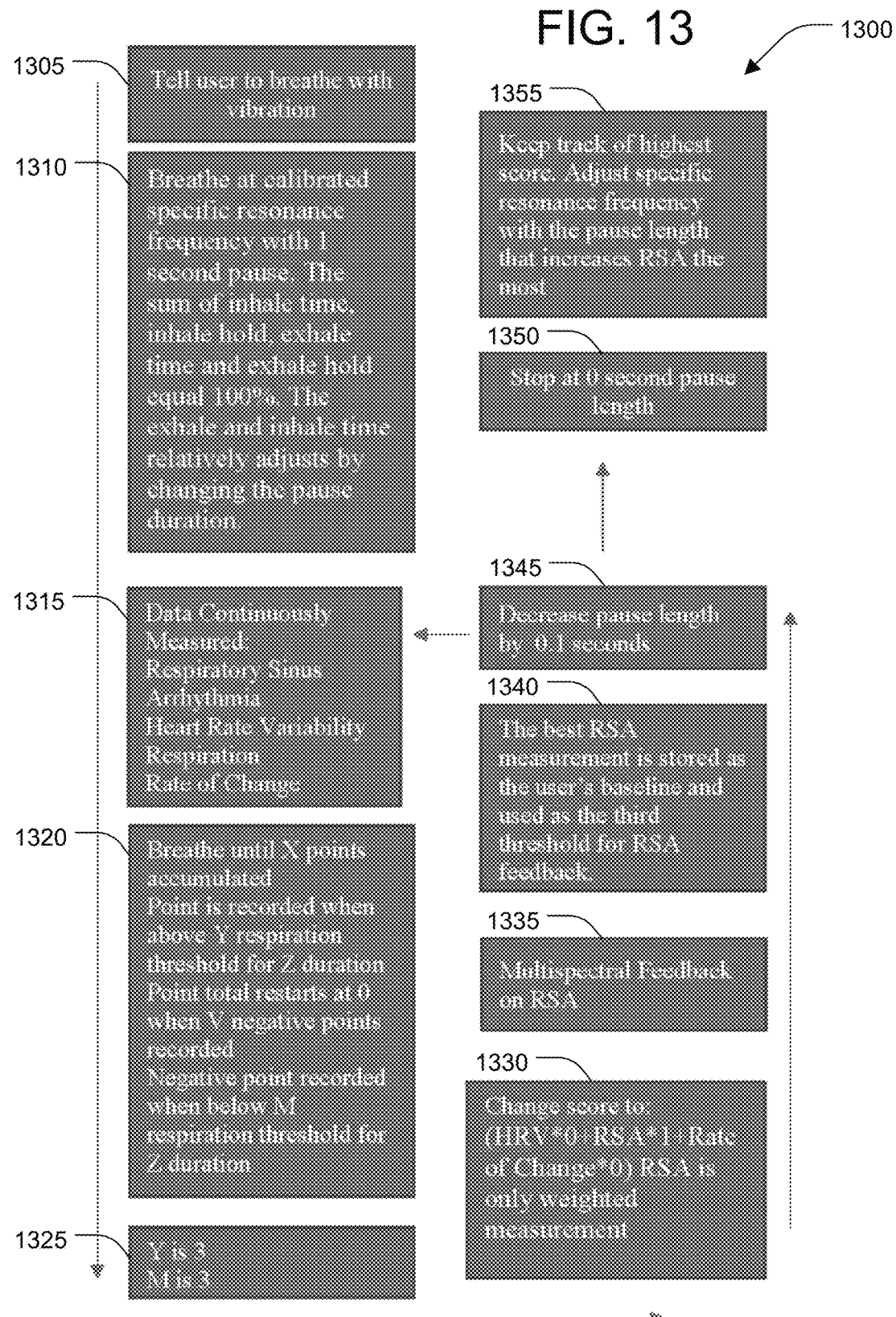
FIG. 13 shows a block diagram illustrating a seventh part of the embodiment of FIG. 7 for providing a user with a breathing rate that is calibrated to the user's resonance breathing frequency.

FIG. 13 shows a seventh method part of the method for providing a user with a breathing rate calibrated to the user's resonance breathing frequency. Seventh method part 1300 is generally directed to improving the precision of the determination of the user's lowest VT Score from step 1260 and the directed breathing rate associated with that lowest VT Score—now considered the user's "specific resonance breathing frequency." In step 1305, the user is directed to breathe with an indicating vibration. In step 1310, the user is directed to breathe at the specific resonance breathing frequency, but with a 1 second pause between each inhalation and exhalation. In other words, the sum of the inhale time, inhale hold, exhale time and exhale hold equal 100% of one period of the specific resonance breathing frequency, with the inhale and exhale times each being shortened by the duration of the pause (or "hold"). The exhale and inhale time relatively adjusts by changing the pause duration. In step 1315, during seventh method part 700, respiration rate and heart rate are continuously measured to develop the Respiration Correlation, RSA, HRV, and Rate of Change values, as discussed with reference to step 915. In step 1320, the user is directed to breathe until X points are accumulated, as discussed previously. In step 1325, it is noted that for method part 1300 of the method, points are accumulated based on a Y respiration threshold of 3 and an M respiration threshold of 3. In step 1330, after X points are accumulated, a VT Score is created based on the equation: HRV*0.0+ RSA*1.0+Rate of Change*0.0, as discussed with regard to step 930. However, note that the VT Score in this step of this embodiment is based solely on the value of RSA, as the weight of the RSA value has been set to 1.0 and the weights of the HRV and Rate of Change values have both been set to zero. In step 1335, it is noted that during method part 1300 of the method, the user is provided multispectral feedback based on the RSA value to help the user achieve the directed breathing rate. In step 1340, the best RSA value recorded (during any step of method part 1300) is stored as the user's baseline RSA and as the third threshold for RSA feedback. In step 1345, the length of the pause is reduced by 0.1 seconds and steps 1315 through 1345 are repeated, stopping after steps 1315 through 1345 have been performed with no pause whatsoever, which is step 1350. In step 1355, the lowest VT Score is determined from the iterations of steps 1315 through 1345. The specific resonance breathing frequency is adjusted to include the pause associated with the lowest VT Score from those iterations.

In the embodiment described above (e.g., with respect to step 1330), RSA becomes weighted higher after conditions are met, with the degree of increase being determined empirically. In an embodiment, the weights in the VT Score may adapt and may in addition be compared to a baseline calculation. In the embodiment, GSR and Temperature are weighted components of the VT Score. In this embodiment, the weights and thresholds are adapted based on a recorded baseline. The recorded baseline is taken when the user is in a stressful state by measuring biometrics when the user is presented with stressful stimuli. Subsequently, the weights and thresholds in each stage will be adapted based on that baseline.

EXAMPLE

The following example illustrates the method of FIGS. 7 through 13.

Steps of the Example that illustrate FIG. 7:
1) User puts on Biometric Analysis Device
2) User breathes at 13 b/m until X points accumulated with breathing feedback
3) User breathes at 11 b/m until X points accumulated with breathing feedback
4) User breathes at 9 b/m until X points accumulated with breathing feedback
5) User breathes at 7 b/m until X points accumulated with breathing feedback
6) User breathes at 5 b/m until X points accumulated with breathing feedback Steps of the Example that illustrate FIG. 8:
7) User breathes at 13 b/m until X points accumulated with breathing feedback
8) User breathes at 11 b/m until X points accumulated with breathing feedback
9) User breathes at 9 b/m until X points accumulated with breathing feedback
10) User breathes at 7 b/m until X points accumulated with breathing feedback
11) User breathes at 5 b/m until X points accumulated with breathing feedback Generally, from this point on, breathing feedback is given for the user for as long as they are not below the third threshold. Additionally, at the start of each breathing rate, the breathing is guided to make sure the user knows how fast to breathe.

Steps of the Example that illustrate FIG. 9:
12) User breathes at 7 b/m until X points accumulated with RSA feedback, VT Score: 0.43.
13) User breathes at 6 b/m until X points accumulated with RSA feedback, VT Score: 0.14.
14) User breathes at 5 b/m until X points accumulated with RSA feedback, VT Score: 0.60.

Steps of the Example that illustrate FIG. 10:
15) Since 6 b/m produced the best (i.e., lowest) VT Score, the user breathes at 6.5 b/m until X points accumulated with RSA feedback, VT Score: 0.1.
16) The user breathes at 5.5 b/m until X points accumulated with RSA feedback, VT Score: 0.4.

Steps of the Example that illustrate FIG. 11:
17) Since 6.5 produced the new best (i.e., lowest) VT Score, the user breathes at 7 b/m until X points accumulated with RSA feedback, VT Score: 0.43.
18) The user breathes at 6 b/m until X points accumulated with RSA feedback, VT Score: 0.14.
19) The user breathes at 6.5 b/m until X points accumulated with RSA feedback, VT Score: 0.1.

Steps of the Example that illustrate FIG. 12:
20) Since 6.5 b/m still produced the best (i.e., lowest) VT Score still, the user breathes at 6.5 b/m until X points accumulated with RSA feedback, a trend shows the user's HR increases before inhalation.
21) Since a trend shows the user's HR increases before inhalation, the user breathes at 6.8 b/m until X points accumulated with RSA feedback, VT Score: 0.13.
22) The user breathes at 6.7 b/m until X points accumulated with RSA feedback, VT Score: 0.12
23) The user breathes at 6.6 b/m until X points accumulated with RSA feedback, VT Score: 0.09.
24) The user breathes at 6.5 b/m until X points accumulated with RSA feedback, VT Score: 0.10.
25) The user breathes at 6.4 b/m until X points accumulated with RSA feedback, VT Score: 0.13.
26) The user breathes at 6.3 b/m until X points accumulated with RSA feedback, VT Score: 0.14.

Steps of the Example that illustrate FIG. 13:
27) Since 6.6 has the lowest VT Score, the user breathes at 6.6 b/m with a 1 second pause duration until X points accumulated with RSA feedback, RSA: 0.15.
28) the user breathes at 6.6 b/m with a 0.9 second pause duration until X points accumulated with RSA feedback, RSA: 0.15.
29) the user breathes at 6.6 b/m with a 0.8 second pause duration until X points accumulated with RSA feedback, RSA: 0.14.
30) the user breathes at 6.6 b/m with a 0.7 second pause duration until X points accumulated with RSA feedback, RSA: 0.13.

31) the user breathes at 6.6 b/m with a 0.6 second pause duration until X points accumulated with RSA feedback, RSA: 0.12.
32) the user breathes at 6.6 b/m with a 0.5 second pause duration until X points accumulated with RSA feedback, RSA: 0.07.
33) the user breathes at 6.6 b/m with a 0.4 second pause duration until X points accumulated with RSA feedback, RSA: 0.09.
34) the user breathes at 6.6 b/m with a 0.3 second pause duration until X points accumulated with RSA feedback, RSA: 0.1.
35) the user breathes at 6.6 b/m with a 0.2 second pause duration until X points accumulated with RSA feedback, RSA: 0.11.
36) the user breathes at 6.6 b/m with a 0.1 second pause duration until X points accumulated with RSA feedback, RSA: 0.16.
37) the user breathes at 6.6 b/m with a 0 second pause duration until X points accumulated with RSA feedback, RSA: 0.17.
38) The Biometric Analysis Device is fully calibrated with an ideal breathing rate of 6.6 b/m and a 0.5 second pause duration.

At step 38 of the example, the Biometric Analysis Device has determined an ideal breathing rate for the user, i.e., the specific resonance breathing frequency of that user, which, when the user breathes at this frequency, will allow the user to attain an optimal resonance state.

After being calibrated according to the embodiment of FIGS. 7 through 13 and the Example, the Biometric Analysis Device may be used to train or direct the user to breathe at that user's specific resonance breathing frequency to attain an optimal resonance state, without having to re-calibrate each time the user wishes to be trained or directed in breathing at their specific resonance breathing frequency.

Figure 14:
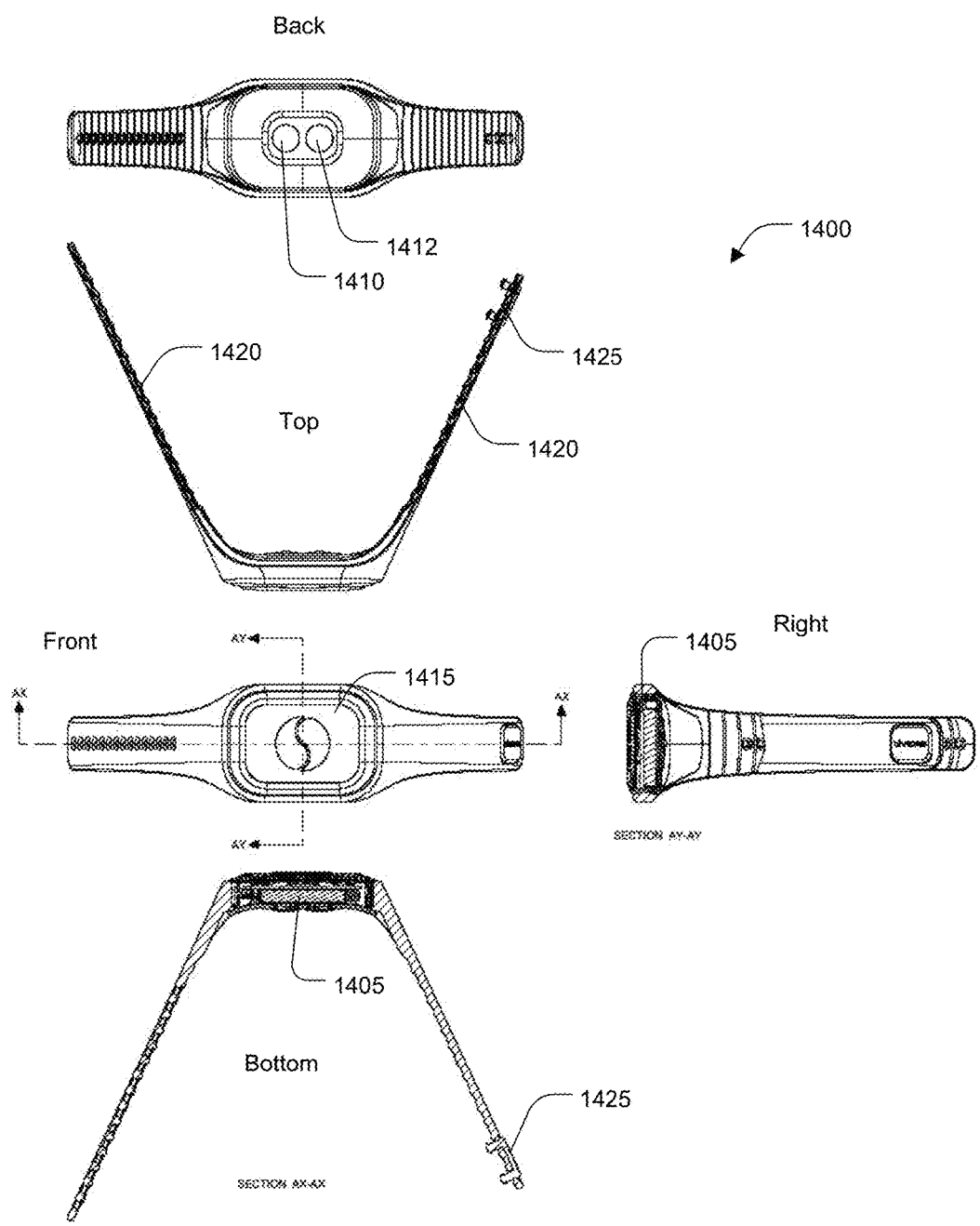
FIG. 14 includes front, back, top, bottom, and right views of an embodiment of a biometric analysis device for implementing embodiments of the methods disclosed herein.

FIG. 14 includes front, back, top, bottom, and right views of an embodiment of a wearable biometric analysis device 1400 for implementing embodiments of the methods disclosed herein. Components and capabilities of biometric analysis device 1400 are also described with reference to system 300 of FIG. 3 and FIG. 4. Biometric Analysis Device 1400 includes a computing device 1405 and a sensor with electrical contacts 1410, 1412 that acquire data that may be used to provide a measure of the user's heart rate and breathing rate. In an embodiment, contacts 1410, 1412 provide data to a TI ADS1292R sensor, which is a low-power, 2-channel, 24-bit analog front-end for biopotential measurements. As such, Biometric Analysis Device 1400 is equipped with both a heart rate sensor and breathing rate sensor. Computing device 1405 is in communication with sensors 1410, 1412. Computing device 1405 is in control of a haptic device (not shown) for communicating with the user. Computing device 1405 includes a display 1415, a user interface, and software, for implementing the steps of the method.

Computing device 1405 receives data from sensors 1410, 1412, performs processing required to implement the steps of the methods, and provides a user interface via display 1415. In some embodiments, all processing required is performed by computing device 1405. In such embodiments, computing device 1405 runs an application for receiving user data, performing the steps of the method, and interacting with the user. In other embodiments, computing device 1405 may be in communication with a server, which performs part of the required processing, with computing device 1405 being an intermediary in communications between the user and the processing server.

As illustrated, Biometric Analysis Device 1400 generally comprises a band 1420 configured to be worn about a wrist of the user. The band 1420 includes an adjustment mechanism 1425, for adjusting a circumference of the band 1420. A user can thus select, using adjustment mechanism 1425, a particular size for positioning band 1420 about the user's wrist. A visual indication, e.g., for feedback, may be provided by display 1415. In an embodiment, visual indicators may be further be positioned on the band 1420 to provide visual signals to the user. Sensors 1410, 1412 are configured to be activated by computing device 1405. In an embodiment, additional sensors, e.g., a temperature sensor or a galvanic response sensor, may be provided to provide more user data for determining vagal tone. In an embodiment, one or more translucent windows may be positioned about the band 1420 to transmit light from one or more indicators positioned with the band 1420.

Biometric analysis device 1400, in one embodiment, is used to lower the user's heart rate by facilitating biofeedback through vibrations transmitted to the user. To this end, biometric analysis device 1400 can operate as a meditation and relaxation tool for users. In particular, a vibration pattern of frequency, duration and magnitude can be selected to encourage a desired behavior. The biofeedback provided to the user by, e.g., display 1415, or haptic device, or speaker, enables the user to self-regulate the user's activity and behavior in order to improve the user's performance or health. Accordingly, the biometric analysis device 1400 provides personal biofeedback customized for the user. The biofeedback allows the user to learn about the user's personal physiological state and physiological responses. By continuously monitoring one or more biometric value, the user can respond to the data received and modify behavior or activity to improve health and performance. By utilizing the biometric analysis device 1400, the user may train their brain to reduce anxiety, stress, depression, and the severity of ADD/ADHD. The computing device 1405 processes biometric data measured by the sensor 1410 and produces feedback correlating to the processed biometric data. The biometric analysis device 1400 thereby provides feedback by sensing and reporting a biometric value measured by the sensor to the user in real time. In one embodiment, real time is less than 1 second, less than 750 milliseconds, less than 500 milliseconds or any other value to provide immediate feedback to the user. The biometric analysis device 1400 is configured to provide the user with feedback with reference to previously-collected biometric data, such as heart rate variability. The biometric analysis device 1400 may emit vibrations based on the user's changing heart rate variability. A visual indication from, e.g., display 1415, can be provided and configured to emit different colors based on when the user is supposed to inhale and exhale for deep breathing relaxation techniques. The user is capable of changing the breathing intervals. The breathing intervals can be adjusted through the user interface to turn on the visual indication.

Figure 15:
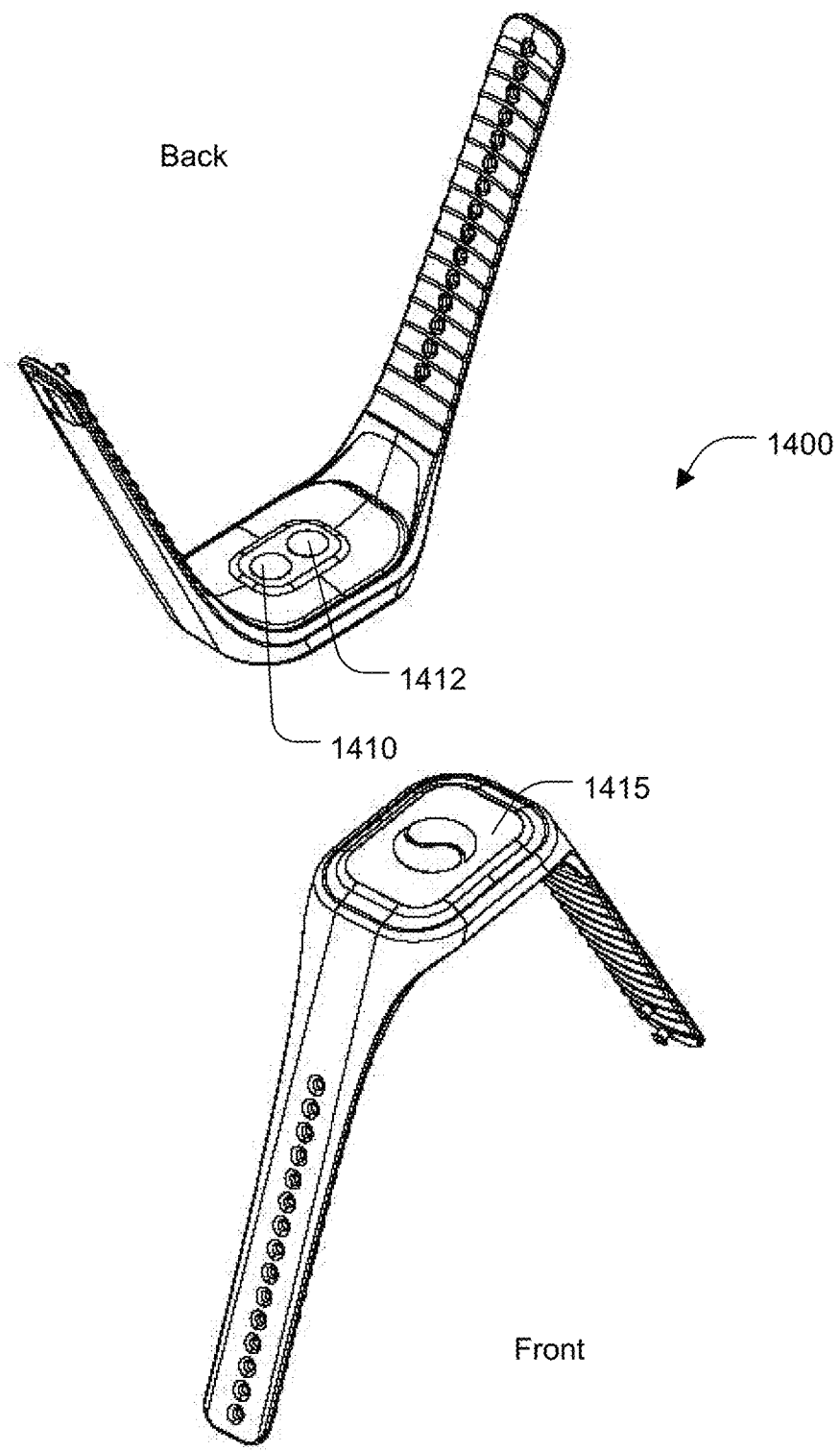
FIG. 15 is a perspective view of the biometric analysis device of FIG. 14.

FIG. 15 is a perspective view of the biometric analysis device of FIG. 14.

FIGS. 14 and 15 illustrate one example embodiment of a wearable biometric analysis device 1400 that is configured to measure and analyze biometric data of a user. In one embodiment, biometric analysis device 1400 can include each of the elements of system 300 of FIG. 3 and FIG. 4. In other embodiments, biometric analysis device 1400 can include other elements that function with biometric analysis device 1400 so as to provide biometric measurement and analysis to assist a user with stress management.

In the description above and throughout, numerous specific details are set forth in order to provide a thorough understanding of an embodiment of this disclosure. It will be evident, however, to one of ordinary skill in the art, that an embodiment may be practiced without these specific details. In other instances, well-known structures and devices are shown in block diagram form to facilitate explanation. The description of the preferred embodiments is not intended to limit the scope of the claims appended hereto. Further, in the methods disclosed herein, various steps are disclosed illustrating some of the functions of an embodiment. These steps are merely examples, and are not meant to be limiting in any way. Other steps and functions may be contemplated without departing from this disclosure or the scope of an embodiment.

What is claimed is:

1. A method for determining a first target respiration frequency for a user, the first target respiration frequency intended to improve a vagal tone of the user, the method comprising:
    providing the user with a first indication to breathe at a pre-determined respiration frequency for each of a first plurality of time periods, each of the first plurality of time periods having a pre-determined respiration frequency that is unique among the pre-determined respiration frequencies for the first plurality;
    using a first sensor, taking first measurements of the user for each of the first plurality of time periods;
    determining, from the first measurements taken of the user, a first heart rate variability value for each of the first plurality of time periods;
    using a second sensor, taking second measurements of the user for each of the first plurality of time periods;
    determining, from the second measurements taken of the user and the first measurements, a first respiratory sinus arrhythmia value for each of the first plurality of time periods;
    combining in whole or in part, for each of the first plurality of time periods, the first heart rate variability value and the first respiratory sinus arrhythmia value to create a first vagal tone value for each of the first plurality of time periods;
    comparing the created plurality of first vagal tone values to each other to determine a first optimal vagal tone value; and
    setting a first target respiration frequency based on a first respiration frequency from a time period corresponding to the first optimal vagal tone value, the first respiration frequency selected from the first pre-determined respiration frequency or a first actual respiration frequency.

2. The method of claim 1 further comprising:
    determining, from the second measurements taken of the user, the first actual respiration frequency for each of the first plurality of time periods;
    determining, based on a comparison of the first actual respiration frequency to the first pre-determined respiration frequency for each of the first plurality of time periods, a respiration correlation value for each of the first plurality of time periods, wherein:
    the first vagal tone value is created by combining, for each of the first plurality of time periods, the first heart rate variability value, the first respiratory sinus arrhythmia value, and the respiration correlation value to create the first vagal tone value for each of the first plurality of time periods.

3. The method of claim 2, wherein the first respiration frequency from the time period corresponding to the first optimal vagal tone value is the actual respiration frequency for the time period corresponding to the first optimal vagal tone value.

4. The method of claim 1, wherein a time period of the first plurality of time periods has a first duration, the method further comprising:
    providing to the user a second indication to breathe at a pre-determined respiration frequency for each of a second plurality of time periods, wherein:
        each of the second plurality of time periods has a second duration less than the first duration,
        each of the second plurality of time periods has a pre-determined respiration frequency that is unique among the pre-determined respiration frequencies for the second plurality, and
        one of the second plurality of time periods has a pre-determined respiration frequency that is the first target respiration frequency;
    determining, from third measurements taken of the user, a second heart rate variability value and, determining from the third measurements and from fourth measurements taken of the user a second respiratory sinus arrhythmia value for each of the second plurality time periods;
    combining, in whole or in part, for each of the second plurality of time periods, the second heart rate variability and the second respiratory sinus arrhythmia value to create a second vagal tone value for each of the second plurality of time periods;
    comparing the created plurality of second vagal tone values to each other to determine a second optimal vagal tone value; and
    setting a second target respiration frequency based on a second respiration frequency from a time period corresponding to the second optimal vagal tone value, the second respiration frequency selected from the second pre-determined respiration frequency or a second actual respiration frequency.

5. The method of claim 4 further comprising:
    providing to the user a third indication to breathe at the second target respiration frequency for each of a third plurality of time periods;
    providing to the user, for each breath in each of the third plurality of time periods, an indication to pause breathing for a pre-determined pause duration after each inhalation and after each exhalation, wherein the second target respiration frequency is maintained, and wherein the pre-determined pause duration is different for each of the third plurality of time periods;
    determining, from fifth measurements taken of the user, a third heart rate variability value and, determining from the fifth measurements and from sixth measurements taken of the user a third respiratory sinus arrhythmia value for each of the third plurality time periods;
    combining, in whole or in part, for each of the third plurality of time periods, the third heart rate variability and the third respiratory sinus arrhythmia value to create a third vagal tone value for each of the third plurality of time periods;
    comparing the created plurality of third vagal tone values to each other to determine a third optimal vagal tone value; and
    modifying the second target respiration frequency to include a target pause between inhalation and exhalation, the target pause based on the pre-determined pause duration corresponding to the third optimal vagal tone value.

6. The method of claim 1, wherein the determining, from the first measurements taken of the user, a first heart rate variability value comprises:
 determining, from the first measurements, peak valley differences in a heart rate of the user; and
 scaling the determined peak valley differences to vary within a range of zero to one.

7. The method of claim 1, wherein the determining, from second measurements taken of the user and the first measurements, a first respiratory sinus arrhythmia value for each of the first plurality of time periods further comprises:
 creating, from the first measurements taken of the user, a beat difference signal based on beat differences in a heart rate of the user;
 creating, from the second measurements taken of the user, a respiration signal;
 normalizing the beat difference signal and the respiration signal to have a common output range;
 producing a correlation value indicative of a correlation between the normalized beat difference signal and the normalized respiration signal, the correlation value being the first respiratory sinus arrhythmia value.

8. A system for determining a first target respiration frequency for a user, the first target respiration frequency intended to improve a vagal tone of the user, the system including at least one sensor, at least one processor, and memory, the memory including instructions, which when executed by the at least one processor cause the at least one processor to perform operations comprising:
 providing the user with a first indication to breathe at a pre-determined respiration frequency for each of a first plurality of time periods, each of the first plurality of time periods having a pre-determined respiration frequency that is unique among the pre-determined respiration frequencies for the first plurality;
 using a first sensor, taking first measurements of the user for each of the first plurality of time periods;
 determining, from the first measurements taken of the user, a first heart rate variability value for each of the first plurality of time periods;
 using a second sensor, taking second measurements of the user for each of the first plurality of time periods;
 determining, from the second measurements taken of the user and the first measurements, a first respiratory sinus arrhythmia value for each of the first plurality of time periods;
 combining in whole or in part, for each of the first plurality of time periods, the first heart rate variability value and the first respiratory sinus arrhythmia value to create a first vagal tone value for each of the first plurality of time periods;
 comparing the created plurality of first vagal tone values to each other to determine a first optimal vagal tone value; and
 setting a first target respiration frequency based on a first respiration frequency from a time period corresponding to the first optimal vagal tone value, the first respiration frequency selected from the first pre-determined respiration frequency or a first actual respiration frequency.

9. The system of claim 8 further comprising instructions causing the at least one processor to perform operations comprising:
 determining, from the second measurements taken of the user, the first actual respiration frequency for each of the first plurality of time periods;
 determining, based on a comparison of the first actual respiration frequency to the first pre-determined respiration frequency for each of the first plurality of time periods, a respiration correlation value for each of the first plurality of time periods, wherein:
 the first vagal tone value is created by combining, for each of the first plurality of time periods, the first heart rate variability value, the first respiratory sinus arrhythmia value, and the respiration correlation value to create the first vagal tone value for each of the first plurality of time periods.

10. The system of claim 9, wherein the first respiration frequency from the time period corresponding to the first optimal vagal tone value is the actual respiration frequency for the time period corresponding to the first optimal vagal tone value.

11. The method of claim 8, wherein a time period of the first plurality of time periods has a first duration, the system further comprising instructions causing the at least one processor to perform operations comprising:
 providing to the user a second indication to breathe at a pre-determined respiration frequency for each of a second plurality of time periods, wherein:
 each of the second plurality of time periods has a second duration less than the first duration,
 each of the second plurality of time periods has a pre-determined respiration frequency that is unique among the pre-determined respiration frequencies for the second plurality, and
 one of the second plurality of time periods has a pre-determined respiration frequency that is the first target respiration frequency;
 determining, from third measurements taken of the user, a second heart rate variability value and, determining from the third measurements and from fourth measurements taken of the user a second respiratory sinus arrhythmia value for each of the second plurality time periods;
 combining, in whole or in part, for each of the second plurality of time periods, the second heart rate variability and the second respiratory sinus arrhythmia value to create a second vagal tone value for each of the second plurality of time periods;
 comparing the created plurality of second vagal tone values to each other to determine a second optimal vagal tone value; and
 setting a second target respiration frequency based on a second respiration frequency from a time period corresponding to the second optimal vagal tone value, the second respiration frequency selected from the second pre-determined respiration frequency or a second actual respiration frequency.

12. The system of claim 11 further comprising instructions causing the at least one processor to perform operations comprising:
 providing to the user a third indication to breathe at the second target respiration frequency for each of a third plurality of time periods;
 providing to the user, for each breath in each of the third plurality of time periods, an indication to pause breathing for a pre-determined pause duration after each inhalation and after each exhalation, wherein the second target respiration frequency is maintained, and wherein the pre-determined pause duration is different for each of the third plurality of time periods;

determining, from fifth measurements taken of the user, a third heart rate variability value and, determining from the fifth measurements and from sixth measurements taken of the user a third respiratory sinus arrhythmia value for each of the third plurality time periods;

combining, in whole or in part, for each of the third plurality of time periods, the third heart rate variability and the third respiratory sinus arrhythmia value to create a third vagal tone value for each of the third plurality of time periods;

comparing the created plurality of third vagal tone values to each other to determine a third optimal vagal tone value; and modifying the second target respiration frequency to include a target pause between inhalation and exhalation, the target pause based on the pre-determined pause duration corresponding to the third optimal vagal tone value.

13. The system of claim 8, wherein the determining, from the first measurements taken of the user, a first heart rate variability value comprises:

determining, from the first measurements, peak valley differences in a heart rate of the user; and scaling the determined peak valley differences to vary within a range of zero to one.

14. The system of claim 8, wherein the determining, from the second measurements taken of the user and the first measurements, a first respiratory sinus arrhythmia value for each of the first plurality of time periods further comprises:

creating, from the first measurements taken of the user, a beat difference signal based on beat differences in a heart rate of the user;

creating, from the second measurements taken of the user, a respiration signal;

normalizing the beat difference signal and the respiration signal to have a common output range;

producing a correlation value indicative of a correlation between the normalized beat difference signal and the normalized respiration signal, the correlation value being the first respiratory sinus arrhythmia value.

* * * * *